(12) United States Patent
Bonnet-Gonnet et al.

(10) Patent No.: US 8,679,540 B2
(45) Date of Patent: Mar. 25, 2014

(54) PHARMACEUTICAL FORMULATIONS FOR THE PROLONGED RELEASE OF ACTIVE PRINCIPLE(S), AND THEIR APPLICATIONS, ESPECIALLY THERAPEUTIC APPLICATIONS

(75) Inventors: Cécile Bonnet-Gonnet, Lyons (FR); David Chognot, Serpaize (FR); Olivier Soula, Meyzieu (FR); Alain Constancis, Lyons (FR)

(73) Assignee: Flamel Technologies, Venissieux (FR)

( * ) Notice: Subject to any disclaimer, the term of this patent is extended or adjusted under 35 U.S.C. 154(b) by 1459 days.

(21) Appl. No.: 11/808,456

(22) Filed: Jun. 11, 2007

(65) Prior Publication Data

US 2008/0026070 A1    Jan. 31, 2008

Related U.S. Application Data

(60) Provisional application No. 60/812,085, filed on Jun. 9, 2006.

(51) Int. Cl.
| | |
|---|---|
| *A61K 9/14* | (2006.01) |
| *A61K 9/50* | (2006.01) |
| *A61K 39/395* | (2006.01) |
| *A61K 39/00* | (2006.01) |
| *A61K 31/00* | (2006.01) |
| *A61K 38/00* | (2006.01) |

(52) U.S. Cl.
USPC ............... 424/489; 424/130.1; 424/184.1; 424/484; 424/488; 424/499; 514/1; 514/1.1

(58) Field of Classification Search
None
See application file for complete search history.

(56) References Cited

U.S. PATENT DOCUMENTS

| | | | |
|---|---|---|---|
| 5,904,936 A | 5/1999 | Huille et al. | |
| 6,630,171 B1 * | 10/2003 | Huille et al. | 424/489 |
| 2002/0002217 A1 * | 1/2002 | McCleskey et al. | 523/347 |
| 2006/0099264 A1 * | 5/2006 | Chan et al. | 424/486 |
| 2007/0218142 A1 * | 9/2007 | Bignon et al. | 424/499 |

FOREIGN PATENT DOCUMENTS

| | | |
|---|---|---|
| FR | 2 801 226 | 5/2001 |
| WO | WO 00/30618 | 6/2000 |
| WO | WO 2005/033181 | 4/2005 |
| WO | WO 2005/051416 | 6/2005 |

OTHER PUBLICATIONS

Akiyoshi et al.; J. Controlled Release 54 (1998) 313-320.*
Fuller et al., "A Procedure for the Facile Synthesis of Amino-Acid N-Carboxyanhydrides," *Biopolymers*, 1976, vol. 15, pp. 1869-1871.
H.R. Kricheldorf, "-Amino Acid N-Carboxy Anydride and Related Heterocycles," *Springer-Verlag, Berlin Heidelberg 1987*.
Tomida et al., "Convenient Synthesis of High Molecular Weight Poly(Succinimide) by Acid-Catalysed Polycondensation of L-aspartic Acid," *Elsevier Science* 1997, vol. 38, pp. 4733-4736.
Gatlin et al., "Formulation and Administration Techniques to Minimize Injection Pain and Tissue Damage Associated with Parenteral Products," *Injectable Drug Development*, 1999, pp. 401-421, eds. P. K. Gupta and G. A. Brazeau, Interpharm Press, Denver, Colorado.

* cited by examiner

Primary Examiner — Robert A Wax
Assistant Examiner — Jeffrey T Palenik
(74) Attorney, Agent, or Firm — Patton Boggs LLP

(57) ABSTRACT

The present invention relates to novel pharmaceutical formulations based on aqueous colloidal suspensions for the prolonged release of one or more active principles, and to the applications, especially therapeutic applications, of these formulations. Formulations may include an aqueous colloidal suspension of low viscosity based on micrometric particles of a water-soluble, biodegradable, amphiphilic polymer carrying hydrophobic groups and ionizable hydrophilic groups that are at least partially ionized, said particles being capable of associating spontaneously and non-covalently with an active principle, at pH=7.0, under isotonic conditions. This suspension contains multivalent ions of opposite polarity to that of the hydrophilic groups, the ratio r, defined by the formula $r = n \times ([IM]/[GI])$, where n is the valency of said multivalent ions, [IM] is the molar concentration of multivalent ions, [GI] is the molar concentration of ionizable groups GI, being between 0.3 and 10.

35 Claims, 1 Drawing Sheet

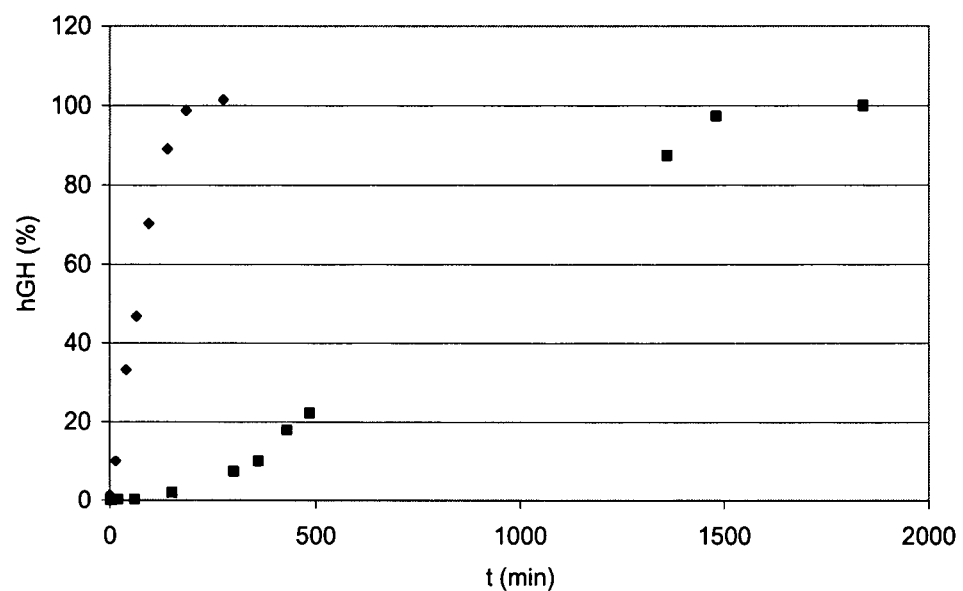

PHARMACEUTICAL FORMULATIONS FOR THE PROLONGED RELEASE OF ACTIVE PRINCIPLE(S), AND THEIR APPLICATIONS, ESPECIALLY THERAPEUTIC APPLICATIONS

CLAIM FOR PRIORITY

This application claims priority to U.S. Provisional Application No. 60/812,085, filed on Jun. 9, 2006, which is herein incorporated by reference in its entirety.

The present invention relates to novel pharmaceutical formulations based on aqueous colloidal suspensions for the prolonged release of one or more active principles AP, particularly protein and peptide active principles, and to the applications, especially therapeutic applications, of these formulations.

These pharmaceutical formulations apply to both human and veterinary therapeutics.

In the field of the prolonged release of pharmaceutical AP, especially therapeutic proteins, there is a need in many cases to ensure as far as possible that the patient's plasma protein or peptide concentration is close to the value observed in the healthy subject.

This objective is compromised by the short life of proteins in the plasma, which makes it necessary to inject the therapeutic protein repeatedly. The plasma concentration of therapeutic protein then has a "sawtooth" profile characterized by high concentration peaks and very low concentration minima. The concentration peaks, which are very much greater than the basal concentration in the healthy subject, have very pronounced harmful effects due to the high toxicity of therapeutic proteins such as the interleukin IL2. Furthermore, the concentration minima are below the concentration that is necessary to have a therapeutic effect, so the patient receives poor therapeutic cover and suffers serious long-term consequences.

Also, to ensure that the patient's plasma concentration of therapeutic protein is close to the ideal value for his treatment, the pharmaceutical formulation in question has to allow the prolonged release of the therapeutic protein so as to limit the variations in plasma concentration over time.

Furthermore, this active formulation should preferably satisfy the following specifications already familiar to those skilled in the art:
1—prolonged release of an active and non-denatured therapeutic protein, e.g. human or synthetic protein, so that the plasma concentration is maintained at the therapeutic level;
2—sufficiently low injection viscosity to be easily injectable;
3—biocompatible and biodegradable form;
4—form exhibiting neither toxicity nor immunogenicity;
5—form having an excellent local tolerance.

In an attempt to achieve these objectives, one of the best approaches proposed in the prior art was to develop forms for the prolonged release of therapeutic protein(s) that consisted of low-viscosity liquid suspensions of nanoparticles loaded with therapeutic proteins. These suspensions facilitated the administration of native therapeutic proteins.

Thus, Flamel Technologies has proposed a method in which the therapeutic protein is associated with nanoparticles of a copolyamino acid comprising hydrophobic groups and hydrophilic groups.

U.S. Pat. No. 5,904,936 describes submicronic particles (NPV), with a mean size of between 0.01 and 0.5 µm, and micrometric particles (MPV), with a mean size of between 0.5 and 20 µm, of an amphiphilic polyamino acid copolymer comprising at least two types of amino acid, one being neutral and hydrophobic and the other being ionizable. Proteins such as insulin are spontaneously adsorbed onto these particles in aqueous solution. The polyamino acid copolymer is e.g. a block copolymer of poly(L-leucine-block-sodium L-glutamate). Said patent describes the aggregation of NPV into MPV by adding monocationic salts (ammonium sulfate) or polycationic salts ($Fe^{2+}$, $Fe^{3+}$, $Zn^{2+}$, $Ca^{2+}$, $Al^{2+}$, $Al^{3+}$ or $Cu^{2+}$), an acid (HCl) or cationic polymers (polylysine) to a colloidal suspension of poly-Leu/Glu.

Patent application WO-A-2005/033181 discloses linear, amphiphilic, anionic homopolyamino acids which comprise aspartic units or glutamic units and whose ends carry hydrophobic groups containing from 8 to 30 carbon atoms. In particular, the "hydrophobically modified" telechelic homopolyamino acids are e.g. a poly[GluONa] with PheOC18/C18 ends or a poly[GluONa] with PheOC18/alpha-tocopherol ends. In water, these "hydrophobically modified" telechelic homopolyamino acids spontaneously form a colloidal suspension of nanoparticles which are easily capable of associating, in aqueous suspension at pH 7.4, with at least one active protein (insulin).

The in vivo release time of the active protein(s) (e.g. insulin) "vectorized" by the suspensions according to U.S. Pat. No. 5,904,936 & WO-A-2005/033181 could profitably be increased.

An increase in release time has been partially achieved by the pharmaceutical forms described in PCT application WO-A-05/051416. In said patent application, a hydrophobically modified colloidal suspension of nanoparticles (0.001-0.5 µm) of poly(sodium L-glutamate) is injected at a concentration such that, after subcutaneous injection, a gel forms in situ in the patient on contact with the endogenous serum albumin. The protein is then released slowly, typically over a period of one week. However, when the concentration of therapeutic protein to be administered is relatively high, as is the case of human growth hormone, for example, the release time is limited to only a few days.

Whatever the case may be, none of this prior art relating to colloids of nanoparticles or microparticles of hydrophobically modified polyamino acids discloses a formulation that makes it possible:
(I) to increase the release time of the active protein after parenteral injection, e.g. subcutaneous injection, particularly when the protein concentration is high,
(II) and/or to reduce the plasma concentration peak of the active protein after injection of the formulation containing it.

Under these conditions, one of the objects of the present invention is therefore to propose a pharmaceutical formulation for the prolonged release of AP which overcomes the deficiencies of the prior art and, in particular, makes it possible, after parenteral (e.g. subcutaneous) injection, to obtain a prolonged in vivo release time for non-denatured AP (e.g. therapeutic proteins and peptides and small molecules), e.g. human or synthetic proteins.

Another object of the invention is to propose a pharmaceutical formulation which makes it possible, after parenteral (e.g. subcutaneous) injection, to obtain a prolonged in vivo release time for highly concentrated therapeutic proteins and peptides, e.g. those containing several mg/ml.

Another object of the invention is to propose a pharmaceutical formulation for the prolonged release of AP in vivo which is stable on storage in both physicochemical and biological terms.

Another object of the invention is to propose a pharmaceutical formulation for the prolonged release of AP in vivo which has at least one of the following properties: biocompatibility, biodegradability, atoxicity, good local tolerance.

Another object of the invention is to propose a pharmaceutical formulation for the slow prolonged release of AP in vivo, said formulation comprising micrometric particles of polymer PO that are auto-associated or auto-associable with at least one AP, PO being a water-soluble biodegradable polymer carrying hydrophobic groups (GH) and ionizable groups (GI), and spontaneously forming a suspension of colloidal nanoparticles in water.

Another object of the invention is to propose a pharmaceutical formulation comprising micrometric particles of the polymer PO vide supra which, after subcutaneous injection, is capable of releasing a therapeutic protein or peptide over a longer time than the release time obtained after administration of the same protein mixed in an aqueous medium of the AP with the colloidal suspension of the polymer PO.

Another object of the invention is to propose a pharmaceutical formulation for the slow prolonged release of AP in vivo, this formulation comprising micrometric particles of polymer PO that are auto-associated with at least one AP, the polymer PO being e.g. a polyamino acid whose main chain is made up of aspartic residues and/or glutamic residues, at least some of these residues being modified by the grafting of at least one hydrophobic group GH in the chain and/or at the end of the chain, PO also being biodegradable, water-soluble and amphiphilic.

Another object of the invention is to propose products derived from the formulation and/or precursors of the formulation referred to in the objects listed above.

It is to the Applicant's credit to have discovered that the aggregation of the nanoparticles of the formulation according to WO 05/051416 into micrometric particles containing multivalent ions of opposite polarity to that of the groups GI, in well-defined proportions, leads to the selection of a specific population of microparticles that allows a significant prolongation of the release time of the AP (e.g. protein or peptide) with which these microparticle are associated.

It is also to the Applicant's credit to have discovered that certain multivalent ions lead to an excellent tolerance of the formulations according to the invention.

The invention therefore relates to a liquid pharmaceutical formulation for the prolonged release of AP which comprises an aqueous colloidal suspension of low viscosity based on micrometric particles of polymer (PO), i. the polymer PO
   being a water-soluble, biodegradable, amphiphilic copolymer carrying hydrophobic groups (GH) and ionizable hydrophilic groups (GI) that are at least partially ionized,
   and spontaneously forming a colloidal suspension of nanoparticles in water, at pH 7.0, under isotonic conditions,
ii. said particles being capable of associating spontaneously and non-covalently with at least one active principle (AP), at pH 7.0, under isotonic conditions, formulation which is characterized in that the micrometric particles of PO have a size, measured in a test T, of between 0.5 and 100 μm, preferably of between 1 and 70 μm and particularly preferably of between 2 and 40 μm, and in that it contains multivalent ions having a valency less than or equal to 4, preferably divalent ions, trivalent ions or mixtures thereof, of opposite polarity to that of the groups GI of the polymer, said multivalent ions having been added in order to cause the nanoparticles of polymer to agregate into micrometric particles in an amount such that the ratio r, measured in a test M, and defined by the formula $$r = n \times \frac{[IM]}{[GI]},$$

where
  n is the valency of said multivalent ions,
  [IM] is the molar concentration of multivalent ions,
  [GI] is the molar concentration of ionizable groups GI,
is between 0.3 and 10, preferably between 0.6 and 5.0 and particularly preferably between 0.8 and 3.0.

These micrometric particles selected according to the invention are produced by the aggregation of a large number of nanoparticles of amphiphilic copolymer. This aggregation is advantageously caused by the presence of multivalent ions of opposite polarity to that of the ionizable groups GI (at least partially ionized) carried by the copolymer. By complexing with polymer chains belonging to distinct nanoparticles, these multivalent ions of opposite polarity to that of the groups GI of the copolymer cause the nanoparticles of polymer to flocculate into microparticles.

The AP can associate spontaneously with the nanoparticles of copolymer PO before they aggregate into micrometric particles, and/or they can associate spontaneously with the micrometric particles during and/or after aggregation.

Moreover, the formulations according to the invention are non-toxic and have a good local tolerance.

Throughout the present disclosure, as distinct from the microparticles having a micrometric size of the formulation according to the invention, the term "submicronic particles" or "nanoparticles" denotes particles whose size (measured in a test T' described below) is greater than or equal to 1 nm and less than 500 nm and preferably between 5 and 250 nm.

For the purposes of the invention, the term "protein" denotes either a protein or a peptide, whether it be an oligopeptide or a polypeptide. This protein or peptide may or may not be modified, e.g. by the grafting of one or more polyoxyethylene groups.

The active principle is designated by the reference AP throughout the present disclosure; AP denotes at least one active principle.

For the purposes of the invention and throughout the present disclosure, the terms "association" and "associate" employed to qualify the relationships between one or more AP and the polymers PO (e.g. polyamino acids) denote that the AP(s) is (are) bonded to the polymer(s) PO non-covalently, e.g. by electrostatic and/or hydrophobic interaction and/or hydrogen bonding and/or steric hindrance.

Test T for Measuring the Size of the Microparticles by Laser Diffraction a—Test T1 in the Case where the Microparticles are in the Form of an Aqueous Dispersion 1 Equipment and Operating Conditions

| | |
|---|---|
| Laser granulometer | Malvern Mastersizer 2000 |
| Module | Hydro 2000SM wet sample dispersion unit |
| Volume of dispersing carrier fluid | 150 ml |
| Wavelengths (blue and red) | 466 and 632 nm |
| Speed of agitation | 2400 rpm |
| Analytical range | 0.02 μm to 2000 μm |
| Optical model (Mie's theory) Values of refractive indices used: | |
| Dispersing fluid (water) | $m_{fluid} = 1.33 + i.0$ |
| Polystyrene latex | $m_{polystyrene\ latex} = 1.59 + i.0$ |
| Obscuration values for triggering analysis | between 5% and 20% |
| Acquisition time | 10 s |

2 Preparation of the Sample

The sample for analysis is prepared by diluting 400 μl in a 5 ml test tube with 600 μl of demineralized water and then agitating the preparation in a Vortex for 10 s (10±5).

3 Analysis of the Sample

The circulating fluid stored in the wet sample dispersion system at rest is emptied out and replaced with fresh demineralized water. The speed of agitation of the Hydro 2000SM unit is set to 2400 rpm.

The measurement is started under the experimental conditions mentioned above:
1—Alignment of the laser beam
2—Recording of the background noise After these steps the operator introduces the sample for analysis in the following manner: dropwise addition of the diluted sample (with a Pasteur pipette) until the obscuration is between 5% and 20%, and initiation of acquisition.

The data are obtained relative to the D50, which is the diameter below which 50% of the analyzed objects are found.

Three measurements of the D50 are made on 3 different preparations and their mean is taken.

b—Test T2 in the Case where the Microparticles are in the Dry Form

1 Equipment and Operating Conditions

| | |
|---|---|
| Laser granulometer | Malvern Mastersizer 2000 |
| Module | Hydro 2000SM wet sample dispersion unit |
| Volume of dispersing carrier fluid | 150 ml |
| Wavelengths (blue and red) | 466 and 632 nm |
| Speed of agitation | 2000 rpm |
| Analytical range | 0.02 μm to 2000 μm |
| Optical model (Mie's theory) | |
| Values of refractive indices used: | |
| Dispersing fluid (water) | $m_{fluid} = 1.39 + i.0$ |
| Polystyrene latex | $m_{polystyrene\ latex} = 1.59 + i.0$ |
| Obscuration values for triggering analysis | between 5% and 20% |
| Acquisition time | 10 s |

2 Preparation of the Sample

A 0.1% solution of Span 80 in heptane is prepared (by weighing out 0.01 g of powdered Span 80 into a 20 ml flask and then adding heptane to a final weight of 10 g). About 6 mg of powder are weighed out into a 5 ml test tube. 0.7 g of heptane containing 0.1% of Span 80 is added to the test tube.

The test tube is placed in an ultrasound bath for 2 minutes to disperse the powder thoroughly.

3 Analysis of the Sample

The circulating fluid stored in the wet sample dispersion system at rest is emptied out and replaced with heptane. The speed of agitation of the Hydro 2000SM unit is set to 2000 rpm.

The measurement is started under the experimental conditions mentioned above:
1—Alignment of the laser beam,
2—Recording of the background noise.

After these steps, the operator introduces the sample for analysis in the following manner: dropwise addition of the diluted sample (with a Pasteur pipette) until the obscuration is between 5% and 20%, and initiation of acquisition.

The data are obtained relative to the D50, which is the diameter below which 50% of the analyzed objects are found.

Three measurements of the D50 are made on 3 different preparations and their mean is taken.

Test T' for Measuring the Size of the Nanoparticles by Quasi-elastic Light Scattering The mean hydrodynamic diameter of the particles of polymer PO according to the invention is measured by the procedure Md defined below:

The solutions of PO are prepared at concentrations of 1 or 2 mg/ml in 0.15 M NaCl medium and agitated for 24 h. These solutions are then passed through a 0.8-0.2 μm filter before being analyzed by dynamic light scattering using a Malvern Compact Goniometer System operating with a vertically polarized He—Ne laser beam of wavelength 632.8 nm. The hydrodynamic diameter of the nanoparticles of polymer PO is calculated from the electric field autocorrelation function by the summation method, as described in the book "Surfactant Science Series" volume 22, Surfactant Solutions, Ed. R. Zana, chap. 3, M. Dekker, 1984.

Test M for Measuring the Multivalent Ion Content by Ion Chromatography

Quantification of the multivalent ion $Mg^{2+}$ will be taken as an example. The method is substantially the same for determining the other cations (only the controls change).

1 Equipment and Reagents

Ion Chromatograph

Dionex ICS2500 ion chromatography system equipped with a conductivity detector, a cation self-regenerating suppressor and a thermostatted oven Column (Dionex): Ion Pac CS16 5×250 mm column Guard column (Dionex): Ion Pac CG16 5×50 mm guard column Cation suppressor (Dionex): CSRS—ULTRA II-4 mm Plastic bottle for ion chromatography (Dionex)

Demineralized water (MilliQ)

0.1 N hydrochloric acid (HCl) (Riedel de Haën)

Methanesulfonic acid (MSA) (ALDRICH)

Sulfate of the multivalent ion: e.g. $MgSO_4$ (Aldrich)

2 Preparation of the Solutions

Solvent: 0.01 N HCl 100 ml of 0.1 N HCl are introduced into a 1 liter flask containing about 500 ml of MilliQ water. The volume is made up to 1 liter with MilliQ water and the solution is stirred magnetically.

Mobile phase: 30 mM MSA

Using a graduated cylinder, 2 liters of MilliQ water are introduced into a 2 liter plastic bottle for ion chromatography. 3.89 ml of MSA are added with an automatic pipette.

The flask is placed in the apparatus and helium bubbling is started in order to mix and degas the phase.

3 Preparation of the Controls and the Samples

Preparation of the Controls

Three controls are prepared in an $Mg^{2+}$ concentration range of 1 mg/l to 2.6 mg/l.

| | | $MgSO_4$ | 0.01 N HCl | |
|---|---|---|---|---|
| SM1 | 100 ml flask | 50 mg | Make up to 100 ml | Magnetic stirring |
| SM2 | 100 ml flask | 80 mg | Make up to 100 ml | Magnetic stirring |
| SM3 | 100 ml flask | 130 mg | Make up to 100 ml | Magnetic stirring |

Dilutions of the stock solutions are prepared.

|    | SMx         | 0.01 N HCl         |
|----|-------------|--------------------|
| T1 | 100 ml flask | 1 ml | Make up to 100 ml |
| T2 | 100 ml flask | 1 ml | Make up to 100 ml |
| T3 | 100 ml flask | 1 ml | Make up to 100 ml |

Preparation of the Samples

The microparticle formulations are agitated thoroughly on a Vortex just before sampling, and mixed with the automatic pipette.

At least one dilution is effected by adapting the weight and dilution volume to give an expected $Mg^{2+}$ concentration of between 1 mg/l and 2.6 mg/l.

Dilution is effected in 0.01 N HCl in order to precipitate the polymer.

Successive dilutions are effected if necessary.

The solution is stirred magnetically for at least 30 minutes.

It is passed through a 0.45 μm filter before being transferred to a flask.

Two preparations are carried out per sample.

4 Conditions of Ion Chromatography

| | |
|---|---|
| Injection volume | 25 μl |
| Flow rate | 1 ml/min |
| Analysis time | 25 min |
| Detection | conductivity in μS/min |
| Eluent | 30 mM MSA |
| Column temperature | 40° C. |
| Suppressor | cation |
| Current | 87 mA |

5 Processing of the Results

Determination of the Calibration Line

The regression line is obtained by considering all the controls in the sequence. The correlation coefficient must be >0.99.

The equation of the line is as follows:

$$Y = aX + b$$

where Y=area of the magnesium peak
X=concentration of the control solution (mg/l)

Determination of the Magnesium Ion Content of the Samples $$M = \frac{(Y_{assay} - b) \times V_d}{a \times P_e}$$

M=$Mg^{2+}$ content (g/l)
$Y_{assay}$=area of the magnesium peak for the assay
a=slope of the calibration line
b=ordinate at the origin of the calibration line
$V_d$=dilution volume (ml)
$P_e$=sample weight (mg)

The final result is the mean of 2 assays. The generally accepted coefficient of variation in ion chromatography is 10%, but this will be confirmed when the method is validated.

Calculation of the Ratio r

In the above protocol we described the determination of the magnesium content. The content T of other multivalent cations ($Ca^{2+}$, $Z^{2+}$, $Al^{3+}$, etc.) is determined in the same way by an analogous method.

Once the value of M has been determined in this way, it is used to deduce the molar concentration of multivalent ion IM:

$$[IM] = \frac{M}{M_{ion}},$$

where $M_{ion}$ is the molecular weight of the multivalent ion in g/mol.

Knowing the structure of the ionizable polymer, particularly its theoretical degree of polymerization DP, its theoretical molecular weight $M_p$ and its hydrophobic grafting rate (i.e. the fraction $\alpha_H$ of groups modified by hydrophobic grafts), it is possible to calculate the molar concentration of ionizable groups for a polymer concentration C (expressed in g/l):

$$[GI] = (1 - \alpha_H) \times \frac{C \times DP}{M_p}$$

This is used to calculate $$r = n \times \frac{[IM]}{[GI]},$$

where n is the valency of the multivalent ion.

Preferably, the formulation according to the invention is characterized in that the micrometric particles have an apparent polymer density $d_{app}$, measured in a test D described below, of between 0.05 and 1.0, preferably of between 0.07 and 0.7 and particularly preferably of between 0.1 and 0.5.

Test D for Measuring the Apparent Density $D_{app}$

The microparticle suspension having a concentration C (mg/g) of polymer PO is homogenized by magnetic stirring. A 2 ml aliquot of microparticle suspension is taken with a micropipette and placed in a previously tared centrifugation tube. The microparticle suspension placed in the tube is then weighed (weight m in g). The tube is placed in a centrifuge and spun for 30 minutes at 8000 rpm. The supernatant is removed with precision using adapted micropipettes. This is used to deduce the volume of sediment $V_{sed}$ (in ml):

$$V_{sed} = V_{tot} - V_{sup}.$$

The apparent polymer density $d_{app}$ (in g/cm³) is given by the formula $$d_{app} = \frac{\frac{m \times c}{1000}}{V_{sed}}$$

The suspension of micrometric particles loaded with AP affords a particularly valuable prolongation of the release time of the AP (e.g. therapeutic protein or peptide) and a reduction of the plasma concentration peak.

In particular, the release time of the AP is significantly increased relative to that of the formulations of the prior art, especially those described in patent application WO 05/051416. The prolongation of the release time of the AP in vivo which is induced by the formulations according to the invention is all the more valuable because the AP (e.g. therapeutic proteins) are still fully bioactive and non-denatured.

Thus, an advantageous functional characteristic of the formulations according to the invention is that the release time $T_r$ of a given AP, as measured in a test L, increases relative to the release time $t_r$ of an identical formulation not containing multivalent ions, as measured in the same test L, this increase preferably being such that $T_r$ is greater than or equal to $1.1 \times t_r$, and particularly preferably such that $T_r$ is greater than or equal to $1.5 \times t_r$.

Test L for Measuring the Release of the AP from the Micrometric Particles According to the Invention 2×2 cm squares are cut out of an absorbent polypropylene material.

The phosphate buffer solution, called PBS, is prepared by dissolving 1 tablet of PBS (Aldrich) in 200 ml of water. This gives 200 ml of a solution containing 0.01 M phosphate buffer+0.0027 M potassium chloride and 0.137 M sodium chloride.

A buffered solution of bovine albumin containing 30 mg/g, called BSA, is prepared by dissolving 6 g of bovine serum albumin, fraction V (SAFC), in 294 g of previously prepared PBS.

Two 50 ml Falcon tubes, one containing PBS and the other BSA solution for soaking the squares of absorbent material, are stored in the refrigerator.

4 or 5 ml of these solutions are placed in hermetic tubes having a capacity of 5 ml (5 samples are provided for each of the two media). They are stored in the refrigerator.

After an interval of 15 hours, the 5 ml tubes containing the continuous phases are placed at 37° C. one hour in advance.

The squares are soaked for one hour, 5 in the PBS and 5 in the BSA (or more if there is a problem on injection), at 37° C.

0.5 ml of formulation is injected with a 27 G needle (1 ml syringe) into the center of each square (parallel to its surface), which has first been sponged lightly on paper.

The injected side is noted.

This procedure is applied to the 10 squares, which will not be immersed in the continuous media until later, so as to synchronize all the kinetics. The squares are placed so that the injected spot is near the top of the tube.

The samples are placed in a holder and are all introduced into a 37° C. oven, with shaking.

The shaking greatly influences the release kinetics and must therefore be controlled: shaking set to 40 with 9 cm between the two obstruction bars.

100 µl aliquots of the continuous phase are taken at different times.

Assay of the Protein by HPLC

Two eluting phases are used:
Phase A: 1260 ml of water/680 ml of acetonitrile/60 ml of THF/1.8 ml of TFA
Phase B: 630 ml of acetonitrile/340 ml of water/30 ml of THF/0.8 ml of TFA The HPLC conditions are collated in the Table below:

| Instrument | Agilent 1100 equipped with: |  |  |
|---|---|---|---|
|  | a cooled automatic sample changer |  |  |
|  | a UV and FLD detector |  |  |
|  | an automatic integrator |  |  |
| Column | Keystone BetaBasic-18 |  |  |
|  | 4.6 × 150 mm |  |  |
|  | 3 µm |  |  |
|  | pore size 150 Å |  |  |
| Gradient | Time (min) | % A | % B |
|  | 0 | 100 | 0 |
|  | 15 | 50 | 50 |
|  | 35 | 10 | 90 |
|  | 36 | 100 | 0 |
|  | 40 | 100 | 0 |
| Analysis time | 40 min (+20 min of washing between injections) |  |  |
| Flow rate | 1.5 ml/min |  |  |
| Column temperature | 38° C. |  |  |
| Sample temperature | Cooled (4° C.) |  |  |
| Injection volume | 100 µl |  |  |
| Detection | UV absorbance at 280 nm |  |  |
|  | Fluorescence at: |  |  |
|  | 296 nm (excitation) |  |  |
|  | 330 nm (emission) |  |  |

The protein concentration in the continuous medium is then plotted as a function of time.

The total amount of protein released is read off from this curve when the latter reaches a plateau for the test to be valid, this value must represent at least 40% of the protein introduced at the start. The time $T_r$, which is the time required to release 50% of the AP introduced, is then read off from this curve.

According to one preferred characteristic, the liquid pharmaceutical formulation according to the invention is characterized in that the micrometric particles of the suspension are obtainable spontaneously in an aqueous liquid by adding a salt containing multivalent ions, preferably divalent ions, of opposite polarity to that of the groups GI of the polymer PO to a suspension of nanoparticles of polymer PO and optionally an AP.

In one preferred embodiment, the formulation according to the invention comprises an AP associated with the microparticles of PO.

This formulation has the advantage of being injectable parenterally and of being liquid under the injection conditions.

According to the invention, the descriptors "liquid", "low viscosity" or "very low viscosity" advantageously correspond to a dynamic viscosity less than or equal to 1000 mPa·s at 20° C. Preferably, the dynamic viscosity of the formulation, measured at 20° C. for a shear gradient of $1000 \text{ s}^{-1}$, is preferably less than or equal to 500 mPa·s and particularly preferably between 2 and 200 mPa·s, e.g. between 1.0 and 100 mPa·s or between 1.0 and 50 mPa·s.

Measurement of the Dynamic Viscosity

The reference measurement for the dynamic viscosity can be made e.g. at 20° C. using an AR1000 rheometer (TA Instruments) equipped with a cone-and-plate geometry (4 cm, 2°). The viscosity v is measured for a shear gradient of $1000 \text{ s}^{-1}$.

This low viscosity makes the formulations of the invention easy to inject parenterally, particularly by the mucosal, intramuscular, subcutaneous, intradermal, intraperitoneal or intracerebral route or into a tumor, inter alia.

The formulation according to the invention can also be administered by the oral, nasal, pulmonary, vaginal, ocular or buccal route.

This liquid state or low viscosity of the formulations of the invention exists both at injection temperatures corresponding to ambient temperatures, e.g. of between 4 and 30° C., and at the physiological temperature.

The polymers PO useful in the invention are water-soluble biodegradable polymers carrying hydrophobic groups GH and ionizable groups GI. The hydrophobic groups can be in reduced number relative to the rest of the chain and can be attached laterally to the chain or intercalated in the chain and be distributed randomly (random copolymer) or distributed in the form of sequences or grafts (block copolymers or sequenced copolymers).

In one preferred embodiment of the invention, the hydrophobic groups GH are attached laterally to the chain.

Without implying a limitation, the hydrophobically modified polymers PO can be selected from the group comprising polyamino acids, (poly)peptides, gelatins, proteins, polysaccharides—preferably selected from the subgroup comprising pullulans and/or chitosans and/or mucopolysaccharides and/or dextrans and/or galactomannans and/or polyhyaluronates—and mixtures thereof.

In one preferred embodiment of the invention, PO is selected from amphiphilic (co)polyamino acids.

For the purposes of the invention and throughout the present disclosure, the term "polyamino acid" covers natural as well as synthetic polyamino acids, together with oligoamino acids comprising from 10 to 20 "amino acid residues" and polyamino acids comprising more than 20 "amino acid" residues.

Preferably, the polyamino acids useful in the present invention are oligomers or homopolymers comprising glutamic or aspartic acid repeat residues or copolymers comprising a mixture of these two types of "amino acid" residues. The residues in question in these polymers are amino acids having the D, L or D/L configuration and are bonded via their alpha or gamma positions in the case of the glutamate or glutamic residue and via their alpha or beta positions in the case of the aspartic or aspartate residue.

The preferred "amino acid" residues of the main polyamino acid chain are those having the L configuration and a linkage of the alpha type.

In one particularly preferred embodiment of the invention, PO is a polyamino acid formed of aspartic residues and/or glutamic residues, at least some of these residues carrying grafts containing at least one hydrophobic group GH. These polyamino acids are especially of the type described in PCT application WO-A-00/30618.

According to a first possibility, the PO of the formulation is (are) defined by general formula (I) below:

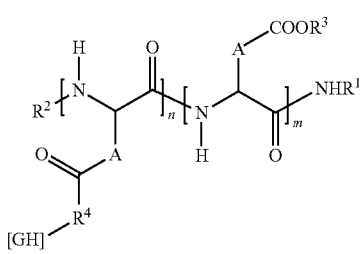

in which:
R$^1$ is H, a linear C2 to C10 or branched C3 to C10 alkyl, a benzyl radical, a terminal residue of amino acid, or —R$^4$-[GH];
R$^2$ is H, a linear C2 to C10 or branched C3 to C10 acyl group, a pyroglutamate or —R$^4$-[GH];
R$^3$ is H or a cationic entity preferably selected from the group comprising:
   metal cations advantageously selected from the subgroup comprising sodium, potassium, calcium and magnesium,
   organic cations advantageously selected from the subgroup comprising:
      cations based on amine,
      cations based on oligoamine,
      cations based on polyamine (polyethylenimine being particularly preferred), and
      cations based on amino acid(s) advantageously selected from the class comprising cations based on lysine or arginine,
   and cationic polyamino acids advantageously selected from the subgroup comprising polylysine and oligolysine;
R$^4$ is a direct bond or a "spacer" based on 1 to 4 amino acid residues;
A independently is a radical —CH$_2$— (aspartic residue) or —CH$_2$—CH$_2$— (glutamic residue);
n/(n+m) is defined as the molar grafting rate and its value is sufficiently low for PO, dissolved in water at pH=7 and at 25° C., to form a colloidal suspension of submicronic particles of PO, n/(n+m) preferably being between 1 and 25 mol % and particularly preferably between 1 and 15 mol %;
(n+m) is defined as the degree of polymerization and varies from 10 to 1000 and preferably between 50 and 300; and
GH is a hydrophobic group.

In one preferred embodiment of the invention, the formulation is characterized in that the hydrophobic group GH is derived from an alcohol precursor selected from the group comprising octanol, dodecanol, tetradecanol, hexadecanol, octadecanol, oleyl alcohol, tocopherol and cholesterol, and in that R$^4$ is a direct bond.

According to a second possibility, the PO of the formulation has (have) one of general formulae (II), (III) and (IV) below:

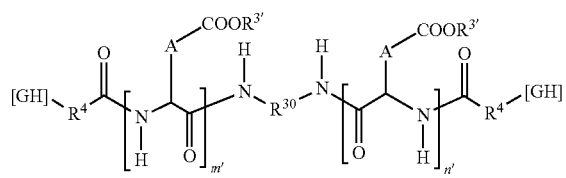

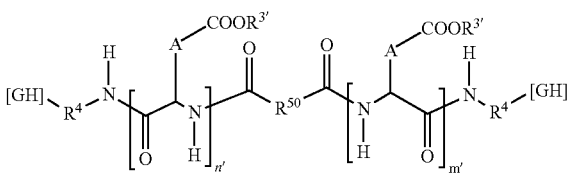

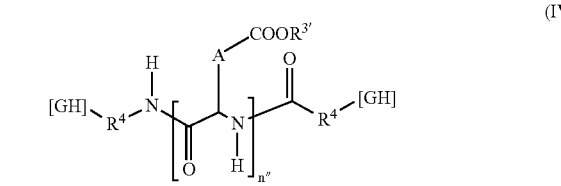

in which:
GH is a hydrophobic group;
R$^{30}$ is a linear C2 to C6 alkyl group;
R$^3$ is H or a cationic entity preferably selected from the group comprising:
   metal cations advantageously selected from the subgroup comprising sodium, potassium, calcium and magnesium, organic cations advantageously selected from the subgroup comprising:
cations based on amine,
cations based on oligoamine,
cations based on polyamine (polyethylenimine being particularly preferred), and
cations based on amino acid(s) advantageously selected from the class comprising cations based on lysine or arginine,
and cationic polyamino acids advantageously selected from the subgroup comprising polylysine and oligolysine;

$R^{50}$ is a C2 to C6 alkyl, dialkoxy or diamine group;
$R^4$ is a direct bond or a "spacer" based on 1 to 4 amino acid residues;
A independently is a radical —CH$_2$— (aspartic residue) or —CH$_2$—CH$_2$— (glutamic residue); and
(n'+m') and n" are defined as the degree of polymerization and vary from 10 to 1000 and preferably between 50 and 300.

Advantageously, the n groups GH of the PO each independently of one another are a monovalent radical of the formula below:

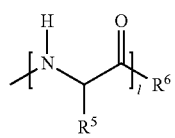

(GH)

in which:
$R^5$ is a methyl (alanine), isopropyl (valine), isobutyl (leucine), sec-butyl
(isoleucine) or benzyl (phenylalanine) radical;
$R^6$ is a hydrophobic radical containing from 6 to 30 carbon atoms; and
l varies from 0 to 6.

According to one noteworthy characteristic of the invention, all or some of the hydrophobic groups $R^6$ of the PO are independently selected from the group of radicals comprising:
a linear or branched alkoxy containing from 6 to 30 carbon atoms and capable of containing at least one heteroatom (preferably O, N or S) or at least one unit of unsaturation,
an alkoxy containing 6 to 30 carbon atoms, having one or more fused carbocyclic rings and optionally containing at least one unit of unsaturation or at least one heteroatom (preferably O, N or S), and
an alkoxyaryl or an aryloxyalkyl having 7 to 30 carbon atoms and capable of containing at least one unit of unsaturation or at least one heteroatom (preferably O, N or S).

In practice and without implying a limitation, the hydrophobic radical $R^6$ of the graft of the PO is derived from an alcohol precursor selected from the group comprising octanol, dodecanol, tetradecanol, hexadecanol, octadecanol, oleyl alcohol, tocopherol and cholesterol.

Advantageously, the main chain of the polyamino acid is:
an alpha-L-glutamate or alpha-L-glutamic homopolymer,
an alpha-L-aspartate or alpha-L-aspartic homopolymer,
or an alpha-L-aspartate/alpha-L-glutamate or alpha-L-aspartic/alpha-L-glutamic copolymer.

Remarkably, the distribution of the aspartic and/or glutamic residues of the main polyamino acid chain of the PO is such that the resulting polymer is either random or of the block type or of the multiblock type.

According to another definition, the PO used in the formulation according to the invention has a molecular weight of between 2000 and 100,000 g/mol and preferably of between 5000 and 40,000 g/mol.

In one variant, the PO of the formulation according to the invention carries at least one graft of the polyalkylene glycol type bonded to a glutamate and/or aspartate residue.

Advantageously, this graft is of the polyalkylene glycol type has formula (V) below:

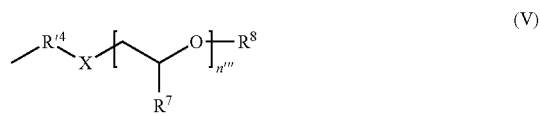

(V)

in which:
$R^4$ is a direct bond or a "spacer" based on 1 to 4 amino acid residues;
X is a heteroatom selected from the group comprising oxygen, nitrogen and sulfur;
$R^7$ and $R^8$ independently are H or a linear C1 to C4 alkyl; and
n''' varies from 10 to 1000 and preferably from 50 to 300.

In practice, the polyalkylene glycol is e.g. a polyethylene glycol.

It is desirable according to the invention for the molar percentage of polyalkylene glycol grafting to vary from 1 to 30%.

The polyamino acids PO are also extremely valuable in that, with an adjustable grafting rate, they disperse in water at pH 7.4 (e.g. with a phosphate buffer) to give colloidal suspensions.

Furthermore, some AP, such as proteins, peptides or small molecules, can associate spontaneously with nanoparticles comprising these polyamino acids PO.

It should be understood that the PO contain ionizable groups which are either neutral (e.g. COOH) or ionized (e.g. COO$^-$), depending on the pH and the composition. For this reason, the solubility in an aqueous phase is a direct function of the proportion of ionized groups and hence of the pH. In aqueous solution, in the case of carboxyl groups, the counterion can be a metal cation such as sodium, calcium or magnesium, or an organic cation such as triethanolamine, tris-(hydroxymethyl)aminomethane or a polyamine like polyethylenimine.

The PO of the polyamino acid type that are capable of being used in the formulation of the invention are obtained e.g. by methods known to those skilled in the art. Random polyamino acids can be obtained by grafting the hydrophobic graft, previously functionalized with the "spacer", directly onto the polymer by a conventional coupling reaction. Block or multiblock polyamino acids PO can be obtained by sequential polymerization of the corresponding amino acid N-carboxy anhydrides (NCA).

For example, a homopolyglutamate or homopolyaspartate polyamino acid or a block, multiblock or random glutamate/aspartate copolymer is prepared by conventional methods.

To obtain a polyamino acid of the alpha type, the most common technique is based on the polymerization of amino acid N-carboxy anhydrides (NCA), which is described e.g. in the article entitled "*Biopolymers*", 1976, 15, 1869, and in the book by H. R. Kricheldorf entitled "*Alpha-amino acid N-carboxy anhydride and related heterocycles*", Springer Verlag (1987). The NCA derivatives are preferably NCA-O-Me, NCA-O-Et or NCA-O-Bz derivatives (Me=methyl, Et=ethyl and Bz=benzyl). The polymers are then hydrolyzed under appropriate conditions to give the polymer in its acid form. These methods are based on the description given in patent FR-A-2 801 226 to the Applicant. A number of polymers that can be used according to the invention, e.g. of the poly(alpha-L-aspartic), poly(alpha-L-glutamic), poly(alpha-D-glutamic) and poly(gamma-L-glutamic) types of variable molecular weights, are commercially available. The polyaspartic polymer of the alpha-beta type is obtained by the condensation of aspartic acid (to give a polysuccinimide) followed by basic hydrolysis (cf. Tomida et al., Polymer, 1997, 38, 4733-36).

Coupling of the graft with an acid group of the polymer is easily effected by reacting the polyamino acid in the presence of a carbodiimide as coupling agent, and optionally a catalyst such as 4-dimethylaminopyridine, in an appropriate solvent such as dimethylformamide (DMF), N-methylpyrrolidone (NMP) or dimethyl sulfoxide (DMSO). The carbodiimide is e.g. dicyclohexylcarbodiimide or diisopropylcarbodiimide. The grafting rate is controlled chemically by the stoichiometry of the constituents and reactants or by the reaction time. The hydrophobic grafts functionalized with a "spacer" are obtained by conventional peptide coupling or by direct condensation under acid catalysis. These techniques are well known to those skilled in the art.

A block or multiblock copolymer is synthesized using NCA derivatives previously synthesized with the hydrophobic graft. For example, the hydrophobic NCA derivative is copolymerized with NCA-O-Bz and the benzyl radicals are then selectively removed by hydrolysis.

The formulations, according to the invention, in the preferred embodiment in which they comprise at least one AP, result from the non-covalent association of nanoparticles based on a PO and at least one AP, in an aqueous liquid medium.

For the preparation, the PO or AP can be in solid form (preferably a powder) or in liquid form (preferably a colloidal aqueous suspension).

In terms of the present disclosure, AP/PO association means that the AP is (are) associated with the polymer(s) PO [e.g. one or more polyamino acids] by one or more bonds other than covalent chemical bonds.

The techniques for associating one or more AP with the PO according to the invention are described in particular in patent application WO-A-00/30618. They consist in incorporating at least one AP into the liquid medium containing nanoparticles of PO to give a colloidal suspension of nanoparticles loaded or associated with one or more AP.

For the purposes of the invention, the term "multivalent ions" denotes divalent ions, trivalent ions, tetravalent ions and mixtures of these ions.

In the case where PO has anionic groups GI, the multivalent ions are multivalent cations, preferably divalent cations and particularly preferably ones selected from the group comprising $Mg^{2+}$, $Ca^{2+}$, $Zn^{2+}$, $Fe^{2+}$, $Cu^{2+}$ and mixtures thereof, and/or trivalent cations selected more particularly preferably from the group comprising $Al^{3+}$, $Fe^{3+}$ and mixtures thereof.

Apart from multivalent ions, the formulation according to the invention can contain monovalent ions (e.g. cations) that may be active in the aggregation of the nanoparticles to microparticles.

These multivalent ions are preferably introduced into the formulation of the invention in the form of an aqueous (organic or mineral) salt solution, e.g. a solution of the sulfate, chloride, acetate, gluconate or glutamate (or other anionic amino acid) of multivalent cations.

To improve its stability, the formulation preferably comprises at least one stabilizer selected from the group comprising:

nanoparticles of at least one polymer PO, PO being a water-soluble, biodegradable, amphiphilic copolymer carrying hydrophobic groups (GH) and ionizable hydrophilic groups (GI) that are at least partially ionized, and spontaneously forming a colloidal suspension of nanoparticles in water, at pH=7.0, under isotonic conditions;

polyalkylene glycols, preferably polyethylene glycols;

copolyalkylene glycols, preferably ethylene glycol/propylene glycol copolymers (of the poloxamer, Pluronic or Lutrol type);

cellulose polymers and derivatives thereof, preferably carboxyalkyl celluloses (e.g. carboxymethyl celluloses) or alkyl celluloses (e.g. methyl celluloses);

esters of sorbitan and one or more fatty acids, preferably esters of polyoxyalkylene (e.g. polyoxyethylene) glycol and at least one acid (e.g. oleic acid), of the Tween or polysorbate type;

surfactants based on phospholipids and polyalkylene glycols, preferably polyethylene glycols;

hydrogenated or non-hydrogenated saccharides such as trehalose, sorbitol, mannitol or sucrose;

polyols such as propylene glycol or glycerol;

gelatins, preferably hydrolyzed gelatins;

nitrogen-containing (co)polymers, preferably from the group comprising polyacrylamides, poly-N-vinylamides, polyvinylpyrrolidones (PVP) and poly-N-vinyllactams;

polyvinyl alcohols (PVA);

and mixtures thereof.

One of the preferred stabilizers according to the invention is made up of nanoparticles of at least one polymer PO which is identical (preferably) or different from the polymer constituting the microparticles.

The amount of stabilizer used in the formulation is preferably between 0.01 and 10% by weight and particularly preferably between 0.1 and 5% by weight.

As regards the stabilizers comprising nanoparticles, these are advantageously used in the formulation in an amount of 1.5 to 3.5% by weight, e.g. of 2.0 to 3.0% ($\approx$2.5%) by weight.

As far as the AP is concerned, this is preferably selected from the group comprising proteins, glycoproteins, proteins bonded to one or more polyalkylene glycol chains [preferably polyethylene glycol (PEG) chains: "PEGylated proteins"], peptides, polysaccharides, liposaccharides, oligonucleotides, polynucleotides and mixtures thereof, and particularly preferably from the subgroup comprising erythropoietin, oxytocin, vasopressin, adrenocorticotropic hormone, epidermal growth factor, platelet-derived growth factor (PDGF), hemopoiesis stimulating factors and mixtures thereof, factors VIII and IX, hemoglobin, cytochromes, prolactin albumins, luliberin, luteinizing hormone releasing hormone (LHRH), LHRH antagonists, LHRH competitors, human, porcine or bovine growth hormones (GH), growth hormone releasing factor, insulin, somatostatin, glucagon, interleukins or mixtures thereof (IL-2, IL-11, IL-12), $\alpha$-, $\beta$- or $\gamma$-interferon, gastrin, tetragastrin, pentagastrin, urogastrone, secretin, calcitonin, enkephalin, endo-morphines, angiotensins, thyrotropin releasing hormone (TRH), tumor necrosis factor (TNF), nerve growth factor (NGF), granulocyte colony stimulating factor (G-CSF), granulocyte macrophage colony stimulating factor (GM-CSF), macrophage colony stimulating factor (M-CSF), heparinase, bone morphogenic protein (BMP), hANP, glucagon-like peptide (GLP-1), VEG-F, recombinant hepatitis B surface antigen (rHBsAg), renin, cytokines, bradykinin, bacitracins, polymixins, colistins, tyrocidine, gramicidines, cyclosporins and synthetic analogs, and pharmaceutically active modifications and fragments of enzymes, cytokines, antibodies, antigens and vaccines.

In one variant, the AP is a "small" hydrophobic, hydrophilic or amphiphilic organic molecule of the type belonging to the anthracycline, taxoid or camptothecin families or of the type belonging to the peptide family, such as leuprolide or cyclosporin and mixtures thereof.

In terms of the present disclosure, a "small" molecule is especially a small non-protein molecule, e.g. a small molecule devoid of amino acids.

In another variant, the AP is advantageously selected from at least one of the following families of active substances: agents for treating alcohol abuse, agents for treating Alzheimer's disease, anesthetics, agents for treating acromegaly, analgesics, antiasthmatics, agents for treating allergies, anticancer agents, anti-inflammatories, anticoagulants and antithrombotics, anticonvulsants, antiepileptics, antidiabetics, antiemetics, antiglaucomas, antihistamines, anti-infectives, antibiotics, antifungals, antivirals, antiparkinsonians, anticholinergics, antitussives, carbonic anhydrase inhibitors, cardiovascular agents, hypolipemics, antiarrhythmics, vasodilators, antianginals, antihypertensives, vasoprotectors, cholinesterase inhibitors, agents for treating central nervous system disorders, central nervous system stimulants, contraceptives, fertility promoters, labor inducers and inhibitors, agents for treating cystic fibrosis, dopamine receptor agonists, agents for treating endometriosis, agents for treating erectile dysfunctions, agents for treating fertility, agents for treating gastrointestinal disorders, immunomodulators and immunosuppressants, agents for treating memory disorders, antimigraines, muscle relaxants, nucleoside analogs, agents for treating osteoporosis, parasympathomimetics, prostaglandins, psychotherapeutic agents, sedatives, hypnotics and tranquilizers, neuroleptics, anxiolytics, psychostimulants, antidepressants, agents for treating dermatological disorders, steroids and hormones, amphetamines, anorexics, non-analgesic painkillers, antiepileptics, barbiturates, benzodiazepines, hypnotics, laxatives, psychotropics and any associations of these products.

From the quantitative point of view, it is particularly valuable if the weight fraction of AP not associated with the micrometric particles [non-associated AP], in %, is such that:
[non-associated AP]≤1,
preferably [non-associated AP]≤0.5.

In one variant, the AP may be the recombinant human growth hormone hGH, having a dose, for example, comprised between 0.2 and 2 mg/kg, and preferably between 0.5 and 1 mg/kg.

In another variant, the AP may be insulin, having a dose, for example, comprised between 0.2 and 2 UI/kg, and preferably between 0.5 and 1 UI/kg.

In another variant, the AP may be interferon α-2b, having a dose, for example, comprised between 20 and 100 μg/kg, and preferably between 40 and 80 μg/kg.

Advantageously, the formulation according to the invention is intended for the preparation of drugs, particularly for administration by the parenteral, mucosal, subcutaneous, intramuscular, intradermal, intraperitoneal or intracerebral route or intratumoral, or by the oral, nasal, pulmonary, vaginal or ocular route.

According to another of its features, the invention relates to a process for the preparation of the above-mentioned formulation.

This process for the preparation of the formulation is characterized in that it consists essentially in:
a. taking or preparing a colloidal suspension of nanoparticles of at least one PO,
b. optionally mixing this colloidal suspension of nanoparticles of PO with at least one AP, preferably in aqueous solution,
c. optionally filtering the resulting suspension,
d. adding multivalent ions (preferably in the form of salt(s)) of opposite polarity to that of the groups GI of the polymer PO, said multivalent ions being added in an amount such that the ratio r,
defined by the formula $$r = n \times \frac{[IM]}{[GI]},$$

where:
n is the valency of said multivalent ions,
[IM] is the molar concentration of multivalent ions,
[GI] is the molar concentration of ionizable groups GI,
is between 0.3 and 10, preferably between 0.6 and 5.0 and particularly preferably between 0.80 and 3.0, and
e. if necessary, adjusting the pH or the osmolarity (e.g. by diafiltration).

The liquid formulations according to the invention are advantageously prepared at room temperature (e.g. 25° C.).

Different modes of association of the AP with the microparticles can be envisaged (vide supra). Advantageously, the AP is associated with the nano-particles that are intended to form the microparticles by aggregation. It is also possible to associate the AP directly with the microparticles. The two methods of association can be combined.

For association with the nanoparticles or microparticles, the AP is advantageously in the form of an aqueous suspension or solution for mixing with the colloidal suspension of nanoparticles or microparticles of PO. In one variant, the AP could be incorporated in solid form and then mixed with the suspension of nanoparticles or microparticles.

The present invention further relates to solid products derived from the nanoparticles and microparticles of PO contained in the formulation according to the invention.

In practice, these derived products can consist especially of powders, gels, implants or films, inter alia.

The invention thus relates to products derived from the formulation according to the invention, taken as such, irrespective of the process for their preparation. The derived product in question is therefore characterized in that it is in non-liquid form and in that it comprises micrometric particles of polymer (PO),
i. the polymer PO
being a water-soluble, biodegradable, amphiphilic copolymer carrying hydrophobic groups (GH) and ionizable hydrophilic groups (GI),
and spontaneously forming a colloidal suspension of nanoparticles in water, at pH=7.0, under isotonic conditions,
ii. said particles being capable of associating spontaneously and non-covalently with at least one AP, at pH=7.0, under isotonic conditions;
these micrometric particles of PO having a size, measured in a test T, of between 0.5 and 100 μm, preferably of between 1 and 70 μm and particularly preferably of between 2 and 40 μm;

and in that it contains derivatives of multivalent ions, preferably divalent ions, of opposite polarity to that of the groups GI of the polymer, the ratio r,
defined by the formula $$r = n \times \frac{[IM]}{[GI]},$$

where
n is the valency of said multivalent ions,
[IM] is the molar concentration of multivalent ions,
[GI] is the molar concentration of ionizable groups GI,
being between 0.3 and 10, preferably between 0.6 and 5.0 and particularly preferably between 0.8 and 3.0.

This derived product can consist e.g. of a powder or a gel.

The present invention further relates to these products derived from the formulation according to the invention as intermediates resulting from the preparation of the formulation according to the invention. The invention therefore further relates to a process for the preparation of at least one of these derived products. This process is characterized in that it consists essentially in drying the suspension of micrometric particles to give a solid form, preferably a powder of micrometric particles, that is capable of being stored or administered.

Such derived products provide access to another method of preparing the formulation according to the invention. The process according to this method is characterized in that it consists essentially in:
taking at least one derived product obtained by the process as defined above,
and reconstituting this derived product by mixing it with water or an aqueous solution S.

In the latter case, the liquid pharmaceutical formulation is reconstituted immediately before use by mixing the solid derived product (e.g. powder) with water or S before injection.

For example, S can comprise an aqueous solution and may simply be water for injectable preparations.

In addition, S can optionally contain:
at least one buffer or at least one injectable salt (phosphate buffer, citrate buffer, sodium chloride) in a concentration e.g. of between 0.001 M and 0.1 M, preferably of between 0.005 M and 0.02 M, this buffer or this injectable salt making it possible to adjust the pH of the solution; and
at least one injectable surfactant, preferably of the polysorbate type, such as Tween® 20 or Tween® 80, or of the poloxamer type, such as Lutrol® F38, Lutrol® F68 or Lutrol® F127, in concentrations e.g. of between 0.01% and 2% and preferably of between 0.05 and 0.5%.

S can also contain densifying agents such as saccharides, namely sucrose, D-mannitol or trehalose, in concentrations of between 0.1% and 10% and preferably of between 0.5 and 5%. The reconstituting solution can also contain an injectable viscosifying polymer selected from the group comprising polysaccharides, synthetic polymers (e.g. sodium carboxymethyl cellulose), polyvinyl alcohol, polyvinylpyrrolidone, polyalkylene glycols (e.g. polyethylene glycols) and mixtures thereof.

More generally, examples of excipients which can be added to the formulation according to the invention are antimicrobials, buffers, antioxidants and isotonicity adjusters known to those skilled in the art. Reference may be made e.g. to the book entitled *Injectable Drug Development*, P. K. Gupta et al., Interpharm Press, Denver, Colo., 1999.

According to the invention, it can be envisaged to make provision for a sterilizing filtration, on filters with a porosity of e.g. 0.2 μm, of the liquid suspension of nanoparticles that gives rise to the micrometric particles of the formulation according to the invention. Aggregation under sterile conditions according to the modes of preparation described above thus enables the formulation to be injected directly into a patient.

The primary properties of the formulation according to the invention include its capacity to release the AP over a prolonged period greater than that obtained with a colloidal suspension of nanoparticles of the same polymer, administered at the same pH, with the same protein concentration and polymer concentration.

The present invention further relates to a process for the preparation of drugs, particularly for administration by the parenteral, mucosal, subcutaneous, intramuscular, intradermal, intraperitoneal or intracerebral route or intratumoral, or by the oral, nasal, pulmonary, vaginal or ocular route, characterized in that it consists essentially in using a formulation as defined above per se, or a formulation obtained by the process also defined above, or any product derived from said formulation, or any precursor of said formulation.

Although the formulation according to the invention is preferably pharmaceutical, this does not exclude cosmetic, dietetic or phytosanitary formulations comprising at least one PO as defined above and at least one AP.

The invention further relates to a method of therapeutic treatment consisting essentially in administering the formulation as described in the present exposure by the parenteral, mucosal, subcutaneous, intramuscular, intradermal, intraperitoneal or intracerebral route or into a tumor, or by the oral, nasal, pulmonary, vaginal or ocular route.

In one particular variant of the invention, this method of therapeutic treatment consists in administering the formulation as described above by injection by the parenteral, subcutaneous, intramuscular, intradermal, intraperitoneal or intracerebral route or intratumoral, preferably in such a way that it forms a depot at the injection site.

The invention will be understood more clearly and its advantages and variants will become clearly apparent from the Examples below, which describe the synthesis of the PO formed of polyamino acids grafted with a hydrophobic group, and their conversion to a system for the prolonged release of AP, namely a formulation according to the invention (stable aqueous colloidal suspension), and demonstrate the ability of such a system not only to associate with a therapeutic protein, but also, in particular, to gel/crosslink in order to release the therapeutic protein in a very prolonged manner in vivo.

DESCRIPTION OF THE SINGLE FIGURE

The single FIGURE is a curve showing the release of human growth hormone [hGH in % relative to the total concentration injected] as a function of time [t in min] in the test L, according to whether it is included in nanoparticles of PO [■ nanoparticles 23 mg/g] or microparticles of PO [♦ microparticles 73 mg/g] prepared according to Example 8.

EXAMPLES

Example 1

Amphiphilic Polymer PO

Synthesis of a Polyglutamate Grafted with Alpha-tocopherol of Synthetic Origin 15 g of an alpha-L-polyglutamic acid (having a molecular weight equivalent to about 16,900 Da, relative to a polyoxyethylene standard, and obtained by the polymerization of NCAGluOMe followed by hydrolysis, as described in patent application FR-A-2 801 226) are solubilized in 288 ml of dimethylformamide (DMF) by heating at 80° C. until the polymer is solubilized. The solution is cooled to 15° C. and 2.5 g of D,L-alpha-tocopherol (>98%, obtained from Fluka®), previously solubilized in 8 ml of DMF, 280 mg of 4-dimethylaminopyridine, previously solubilized in 1 ml of DMF, and 1.6 g of diisopropylcarbodiimide, previously solubilized in 6 ml of DMF, are added in succession. After stirring for 3 hours, the reaction medium is poured into 1200 ml of water containing 15% of sodium chloride and hydrochloric acid (pH=2). The polymer which precipitates is then recovered by filtration and washed with 0.1 N hydrochloric acid, with water and with diisopropyl ether. The polymer is then dried in a vacuum oven at 40° C. to give a yield in the order of 90%. The molecular weight measured by size exclusion chromatography is 15,500, relative to a polyoxyethylene standard. The proportion of grafted tocopherol, estimated by proton NMR spectroscopy, is 5.1 mol %. A suspension of nanoparticles of the polymer in water is obtained by solubilizing it in water, and by adjusting the pH (neutralization of the carboxylates) to 7±1.

Example 2

Preparation of 100 g of a Colloidal Suspension of Nanoparticles of Polymer PO Loaded with hGH 2.1 Preparation of a Colloidal Solution of Amphiphilic Polymer PO The polymer is left to stand in solution overnight to reach a constant temperature of 30° C.

35.3 g of polymer PO of Example 1 are weighed out.

It is diluted with 26.65 g of sterile water for injection (for a polymer PO at a concentration of 28.4 mg/g).

The polymer solution is stirred magnetically.

The osmolarity of the solution is adjusted to 300±20 mOsm by introducing 1.89 g of a 5.13 M aqueous solution of NaCl (30% w/w).

The pH is adjusted to 7.4±0.2 by adding 0.38 g of 1 N NaOH solution.

This gives 64.22 g of a polymer solution containing 15.61 mg/g.

2.2 Association of the Protein with the Polymer

A solution of recombinant human growth hormone, called hGH, is thawed at 25° C. for 90 min.

35.92 g of hGH solution (concentrated, 3.9 mg/g) are then added to 64.15 g of the previously prepared colloidal solution of polymer, with stirring.

The solution loaded with protein is aged for 2 h at room temperature.

It is then passed through a 0.8-0.2 μm filter and allowed to age overnight.

This gives 100 g of a ready-to-inject formulation containing 1.4 mg/g of hGH and 10 mg/g of polymer of the PO type.

Example 3

Preparation of a Suspension of Micrometric Particles Using MgCl$_2$

The suspension is prepared from a solution prepared according to Example 2 with adjusted pH and osmolarity and containing 10.0 mg/g of PO.

a) Flocculation of the solution by adding 1 M MgCl$_2$ solution using a controlled-action syringe delivering about 20 ml/h, with stirring (setting no. 9). The ratio characterizing the addition of cations:

$$r = 2 \times \frac{[Mg^{2+}]}{[Glu]}$$

is equal to 3.36 in this case. A solution containing 8.51 mg/g of PO is obtained.

b) Centrifugation for 25 min at 2500 rpm. The clear supernatant has an osmolarity of 646 mOsm.
c) Washing of the residue with sterile water (⅛ of the volume of initial solution) and centrifugation for 10 min at 2500 rpm. The clear supernatant has an osmolarity of 350 mOsm.
d) Centrifugation for 10 min at 2500 rpm.

This formulation is characterized as follows:

| | |
|---|---|
| pH | 6.64 |
| Osmolality | 349 mOsm |
| [PO] | 50.77 mg/g |
| Particle diameter D50 (according to test T1) | 20 μm |

Example 4

Preparation of a Suspension of Microparticles Produced with CaCl$_2$ and with pH Lowering The suspension is prepared from a solution prepared according to Example 2 having final characteristics of 1.2 mg/g of hGH and 25.9 mg/g of PO.
a) Adjustment of the initial formulation to pH=5.52 with 0.1 N HCl using a controlled-action syringe delivering about 70 ml/h, with stirring (600 rpm).
b) Flocculation of the polymer by adding 1 M CaCl$_2$ solution using a controlled-action syringe delivering about 39 ml/h, with stirring (600 rpm). The ratio characterizing the addition of cations:

$$r = 2 \times \frac{[Ca^{2+}]}{[Glu]}$$

is equal to 1.68 in this case.
c) Centrifugation for 8 min at 2500 rpm. The clear supernatant has a pH of 4.73 and an osmolarity of 653 mOsm.
d) Washing of the residue with MilliQ water (⅛ of the volume of initial solution) and centrifugation for 4 min at 2500 rpm. The clear supernatant has a pH of 4.72 and an osmolarity of 378 mOsm.
e) Concentration of the residue by centrifugation for 4 min at 2500 rpm to give a concentrated suspension.

The suspension obtained has the following characteristics:

| | |
|---|---|
| pH | 4.88 |
| Osmolality | 386 mOsm |
| [PO] | 122.88 mg/g |
| [hGH] | 4.9 mg/g |
| Particle diameter D50 (according to test T1) | 23 μm |

Example 5

Preparation of a Suspension of Microparticles Produced with CaCl$_2$

The suspension is prepared from a solution prepared according to Example 2 having final characteristics of 1.2 mg/g of hGH and 26.01 mg/g of PO.

a) Flocculation of the initial formulation by adding 1 M CaCl$_2$ solution using a controlled-action syringe delivering about 40.3 ml/h, with stirring (600 rpm), until the ratio r is 3.36. This gives a formulation containing 0.93 mg/g of hGH for 20.28 mg/g of PO.
b) Centrifugation for 4 min at 2500 rpm. The clear supernatant has a pH of 6.34 and an osmolarity of 832 mOsm.
c) Washing of the residue with MilliQ water (⅓ of the volume of initial solution) and centrifugation for 8 min at 2500 rpm. The clear supernatant has a pH of 6.56 and an osmolarity of 334 mOsm.
d) Concentration of the residue by centrifugation for 8 min at 2500 rpm to give a concentrated suspension.

This formulation is characterized as follows:

| | |
|---|---|
| pH | 6.25 |
| Osmolality | 343 mOsm |
| [PO] | 101.87 mg/g |
| [hGH] | 4.7 mg/g |
| Particle diameter D50 (according to test T1) | 13 μm |

Example 6

Preparation of a Suspension of Microparticles Produced with ZnCl$_2$

The suspension is prepared from a solution prepared according to Example 2 having final characteristics of 1.4 mg/g of hGH and 10.00 mg/g of PO.

a) Flocculation of the solution by adding 1 M ZnCl$_2$ solution using a controlled-action syringe delivering about 20 ml/h, with stirring (setting no. 9), until the ratio r is 1.54. A solution containing 9.64 mg/g of PO is obtained.
b) Centrifugation for 4 min at 2500 rpm. The clear supernatant has an osmolarity of 389 mOsm.
c) Washing of the residue with sterile water (1/13 of the volume of initial solution) and centrifugation for 8 min at 2500 rpm. The clear supernatant has an osmolarity of 237 mOsm.
d) Washing of the residue with 0.9% NaCl (⅛ of the volume of initial solution). Centrifugation for 8 min at 2500 rpm. The clear supernatant has an osmolarity of 253 mOsm. The calculated theoretical concentration is then 64.97 mg/ml.

This formulation is characterized as follows:

| | |
|---|---|
| pH | 5.86 |
| Osmolality | 256 mOsm |
| [PO] | 63.51 mg/g |
| Particle diameter D50 (according to test T1) | 9 μm |

Example 7

Preparation of a Suspension of Microparticles Produced with MgCl$_2$ Under Conditions 1

The suspension is prepared from a solution prepared according to Example 2 having final characteristics of 0.48 mg/g of hGH and 23.05 mg/g of PO, with adjusted pH and osmolarity.

a) Dilution to 10.0 mg/g with 0.9% NaCl.
b) Flocculation of the solution by adding 1 M MgCl$_2$.6H$_2$O solution using a controlled-action syringe delivering about 20 ml/h, with stirring (setting no. 10), until the ratio r is 6.93. This gives a solution containing 8.59 mg/g of PO.
c) Centrifugation for 10 min at 2500 rpm. The clear supernatant has an osmolarity of 654 mOsm.
d) Washing of the residue with sterile water (1/7 of the volume of initial solution) and centrifugation for 10 min at 2500 rpm. The clear supernatant has an osmolarity of 291 mOsm.

This formulation is characterized as follows:

| | |
|---|---|
| pH | 6.56 |
| Osmolality | 323 mOsm |
| [PO] | 75.7 mg/g |
| [hGH] | 1.3 mg/g |
| Particle diameter D50 (according to test T1) | 8.6 μm |

Example 8

Preparation of a Suspension of Microparticles Produced with MgCl$_2$ Under Conditions 2

The suspension is prepared from a solution prepared according to Example 2 having final characteristics of 1.33 mg/g of hGH and 10.10 mg/g of PO, with adjusted pH and osmolarity.

a) Flocculation of the solution in the presence of a nitrogen sweep by adding nitrogen-bubbled 2 M MgCl$_2$.6H$_2$O solution using a pump delivering about 8 ml/min, with stirring (500 rpm), until the ratio r is 10.01. This gives a solution containing 8.98 mg/g of PO and having an osmolarity of 914 mOsm.
b) Ageing for three hours, with stirring.
c) Use of a Microza module (UJP-0047R—Pall), having a specific surface area of 0.02 m$^2$. This module has first been conditioned (removal of the glycerol and ethanol by soaking in water), depyrogenated (7% NaOH followed by rinsing with water) and autoclaved.
d) Conditioning of the module with MgCl$_2$ solution having an osmolarity of 900 mOsm.
e) Washing with sterile water (1.04 times the volume of flocculated formulation), which is added at a rate of 8 ml/min to keep the overall volume constant. The circulation is assured with a pump at 25% power, maintaining a pressure of 0.3 bar. This step lasts for 3 h. The clear filtrate has a final osmolarity of 459 mOsm.
f) Use of a Microza module (0.02 m$^2$) whose circulation is assured with a pump at 25% power. Concentration with a permeate flow rate of 4.4 ml/min. This step lasts for 160 min. The filtrate has a final osmolarity of 324 mOsm.

This formulation, which is a white fluid suspension, possesses the following characteristics:

| | |
|---|---|
| Osmolality | 329 mOsm |
| [Mg] | 6.8 mg/g |
| [microparticles] | 43.6 mg/g |
| [hGH] | 4.56 mg/g |
| r (according to test M) | 2.30 |
| $T_r$ (according to test L) | 16 h |
| $d_{app}$ (according to test D) | 0.15 |

Example 9

Preparation of a Stable Suspension of Microparticles Produced with $MgCl_2$ Under Conditions 3 a) Preparation of a solution of PO prepared according to Example 2, hereafter called initial formulation hGH 1.4 mg/g/PO 10 mg/g A solution of recombinant human growth hormone is thawed for 2 h at 25° C. ([hGH]=3.9 mg/ml, pH=7.2, 330 mOsm).

The polymer PO is diluted and adjusted (300 mOsm, pH=7.4, 15.6 mg/g).

The solution of hGH is poured onto the polymer, and the hGH/PO mixture (1.4/10 mg/g) is then degassed.

Association is effected overnight at room temperature.

| | | | |
|---|---|---|---|
| PO | M (PO) | 2317.90 | g |
| pH = 7.4 - 300 mOsm | [PO] | 15.61 | mg/g |
| hGH | M (hGH) | 1302.30 | g |
| | [hGH] | 3.9 | mg/g |
| Initial formulation | M | 3497.00 | g |
| | [hGH] | 1.35 | mg/g |
| | [PO] | 10.01 | mg/g | b) Preparation of the microparticles hGH 5 mg/g/Mg microparticles 40 mg/g

The initial formulation is flocculated by the controlled addition of 2 M $MgCl_2$ with a ratio r of 9.01, after which the whole is left to age for 1 h.

The suspension is washed with water by tangential microfiltration (Microza module from Pall with a specific surface area of $0.32\ m^2$) until the osmolality is about 300 mOsm. It is then concentrated to a PO concentration of between 38 and 41 mg/g.

| | | | |
|---|---|---|---|
| Initial formulation | M | 3458.4 | g |
| | [hGH] | 1.399 | mg/g |
| | [PO] | 10.01 | mg/g |
| Flocculation | M ($MgCl_2$, 2 M) | 457.6 | g |
| | Flow rate | 8.47 | g/min |
| | M (suspension) | 3883.4 | g |
| | [PO] | 8.84 | mg/g |
| | Osmolality | 942 | mOsm |
| Washing | M ($H_2O$) | 4241 | g |
| | Flow rate | 42.43 | mg/min |
| | Osmolality | 330 | mOsm |
| Concentration | M (filtrate) | 3157 | g |
| | Flow rate | 39.46 | mg/min |
| | M (concentrated microparticles) | 713.8 | g |
| | [hGH] | 5.28 | mg/g |
| | [PO] | 50.9 | mg/g |
| Dilution | M ($MgCl_2$, 0.1 M) | 179.9 | g |
| | M (concentrated microparticles) | 893.7 | g |
| | [hGH] | 4.22 | mg/g |
| | [PO] | 40.65 | mg/g | c) Preparation of the mixed formulation hGH 5 mg/g/Mg microparticles 40 mg/PO 23 mg/g The microparticles are stabilized by adding the polymer of the PO type in its lyophilized form.

The lyophilizate is added to the suspension, with stirring. The whole is placed under vacuum (30 mbar) until the next day, with stirring.

| | | | |
|---|---|---|---|
| Suspension | M (concentrated microparticles) | 872.5 | g |
| Lyophilized PO | [$H_2O$] | 10.125% | |
| | M added | 23.175 | g |
| Final formulation | M | 895.68 | g |
| | [hGH] | 4.11 | mg/g |
| | [PO in microparticles] | 39.60 | mg/g |
| | [PO added] | 23.00 | mg/g |
| | pH | 6.4 | |
| | Osmolality (mOsm) | 409 | |
| | [Mg] (g/l) | 4.0 | |
| | r (according to test M) | 0.94 | |
| | $d_{app}$ (according to test D) | 0.14 | |
| | $T_r$ (according to test L) | 30.56 | h |

Example 10

Preparation of Dry Micrometric Particles Loaded with hGH from a Suspension of Microparticles by a First Embodiment of the Process According to the Invention Firstly, a suspension of microparticles loaded with hGH is produced under the conditions described in steps a) to e) of Example 8 (flocculation, ageing, washing). The suspension is washed until the osmolality is about 280 mOsm. The suspension, containing about 10 mg/g of polymer, is then lyophilized on a Bioblock ALPHA 1-4 LSC apparatus after having been frozen in liquid nitrogen for 76 h.

Reconstitution and Characterization of the Suspension 1 ml of water for injectable preparations is added to 40 mg of powder. The solution is stirred by hand for a few seconds to effect homogeneous wetting of the powder. The solution is left to stand for about 10 minutes. It is homogenized for a few seconds by manual stirring and withdrawn using a 21 G needle to give 1 ml of a ready-to-inject solution.

The characteristics of the suspension are described below.

| $r = 2 \times \frac{[Mg^{2+}]}{[COO^-]}$ (according to test M) | pH | Osmolality | $d_{app}$(mg/ml) (according to test D) |
|---|---|---|---|
| 1.4 | 6.6 | 338 | 0.10 |

Example 11

Preparation of Dry Micrometric Particles of Polymer Loaded with hGH from a Suspension of Microparticles by a Second Embodiment of the Process According to the Invention Firstly, a Suspension of Microparticles Loaded with hGH is Produced Under the conditions described in steps a) to e) of Example 8 (flocculation, ageing, washing). The suspension is washed until the osmolality is about 280 mOsm. The suspension, containing about 10 mg/g of polymer, is then dried on a Büchi B290 atomization apparatus. The liquid solution is withdrawn at a rate of 5 ml/min and nebulized through a spray nozzle fed with nitrogen (7 bar-500 l/h). The withdrawal rate (drying air) is 40 m³/h. The inlet temperature is kept at 90° C., which induces an outlet temperature of 45° C. under these conditions.

Under these conditions, the size D(0.5) of the particles obtained (according to test T2) is 5 μm (50% of the volume is occupied by particles having a diameter of <5 μm).

Reconstitution and Characterization of the Suspension 1 ml of water for injectable preparations is added to 30 mg of powder. The solution is stirred by hand for a few seconds to effect homogeneous wetting of the powder. The solution is left to stand for about 10 minutes. It is homogenized for a few seconds by manual stirring and withdrawn using a 21 G needle to give 1 ml of a ready-to-inject solution.

The characteristics of the suspension are described below.

| $r = 2 \times \frac{[Mg^{2+}]}{[COO^-]}$ (according to test M) | pH | Osmolality | Size D(0.5) μm (according to test T1) | $d_{app}$(mg/ml) (according to test D) |
|---|---|---|---|---|
| 2.3 | 6.8 | 598 | 10.0 | 0.15 | where:

$C_{max}$ is the maximum serum hGH concentration,

T>5 ng/ml is the time when the serum hGH concentration is greater than 5 ng/ml,

AUC represents the area under the curve of serum hGH concentration as a function of time, RBA represents the bioavailability relative to an Immediate-Release formulation, $T_{50\% \, auc}$ represents the time required to release 50% of the total hGH released.

The hGH IR has a rapid release profile with a maximum serum concentration of 582±155 ng/ml reached after a median time of 2 hours. The hGH is then eliminated fairly rapidly (apparent T½ of about 2 hours) according to a monoexponential decrease. The circulating hGH is then no longer quantifiable beyond 24 hours.

Formulation 1 has a prolonged hGH release profile with a slow absorption phase before reaching comparable maximum serum concentrations (44±6 and 37±4 ng/ml respectively)

Example 12

Pharmacokinetics of hGH in the Dog after Subcutaneous Injection of Various Formulations Based on Amphiphilic Polyamino Acids in the Form of Nanoparticles and Microparticles Twelve naïve beagle dogs (weighing 7 to 10 kg) were treated with the following formulations:

| Formulation | Number of dogs | [hGH] (mg/ml) | [PO] (mg/ml) | Dose (mg/kg) | Dose volume (ml/kg) |
|---|---|---|---|---|---|
| hGH IR | 4 | 4 | 0 | 1 | 0.23 |
| Formulation 1 | 4 | 5 | 22.6 | 1 | 0.22 |
| Formulation 2 | 4 | 5 | 117.5 | 1 | 0.20 |

The hGH IR corresponds to a solution of recombinant human growth hormone ([hGH]=4 mg/ml, pH=7.2, 330 mOsm).

Formulation 1 is prepared according to Example 2 and formulation 2 according to Example 7. The hGH is assayed by ELISA (DSL 10-1900 kit).

The pharmacokinetic data are collated in the Table below:

after a median time of 24 hours. The elimination slope indicates the absence of quantifiable hGH beyond 48 hours (the serum concentration being 4.8±3.1 ng/ml).

This formulation demonstrates in this case a slower release of hGH into the blood compartment, as illustrated by the shift in $C_{max}$ centered around 24 hours. However, this phenomenon does not seem to prolong the presence of the hGH in the serum significantly, since the circulating concentration at 48 hours appears to be zero. The AUC of formulation 1 appears slightly reduced relative to the reference IR: the bioavailability is 80%.

Formulation 2, on the other hand, offers a major modification of the pharmacokinetic profile with a very slow release following a lag time of 4 hours, and then a maximum serum concentration of 25±5 ng/ml reached after a median time of 108 hours (range: 72-168 hours). The general trend of the pharmacokinetics of formulation 2 is a very flat profile in the form of a pseudo-plateau of infusion-like type. The level of circulating hGH returns to an unquantifiable concentration between 168 hours and 240 hours (7 and 10 days). This formulation has a much smaller AUC: 45% loss of relative bioavailability (RBA=55%).

| Formulation | $C_{max}$ ± SD (ng/ml) | T > 5 ng/ml ± SD (h) | $AUC_{0\text{-}last}$ ± SD (ng · h/ml) | RBA (%) | $T_{50\% \, auc}$ ± SD (h) |
|---|---|---|---|---|---|
| hGH IR | 582 ± 155 | 18 ± 3 | 3209 ± 276 | 100 | 4 ± 1 |
| Formulation 1 | 135 ± 37 | 44 ± 6 | 2579 ± 516 | 80 | 25 ± 5 |
| Formulation 2 | 25 ± 5 | 129 ± 26 | 1759 ± 246 | 55 | 121 ± 33 |

Example 13

Pharmacokinetics of hGH in the Dog after Subcutaneous Injection of a Formulation Based on Amphiphilic Polyamino Acids in the Form of Microparticles Twelve naïve beagle dogs (weighing 7 to 10 kg) were treated with the following formulations:

| Formulation | Number of dogs | [hGH] (mg/ml) | [PO] (mg/ml) | pH/ osmolarity | Dose (mg/kg) | Dose volume (ml/kg) |
|---|---|---|---|---|---|---|
| hGH IR | 6 | 4.1 | 0 | 7.4/321 | 5 × 0.1 per day | 0.024 |
| Formulation 3 | 6 | 4.3 | 64.2 | 6.4/409 | 0.5 | 0.122 |

The hGH IR corresponds to a solution of recombinant human growth hormone ([hGH]=4.1 mg/ml, pH=7.2, 330 mOsm). Formulation 3 is prepared according to Example 9.

The pharmacokinetic data are collated in the Table below:

| Formulation | $C_{max} \pm SD$ (ng/ml) | T > 1 ng/ml ± SD (h) | $AUC_{0\text{-}last} \pm SD$ (ng · h/ml) | RBA (%) | $T_{50\% \, auc} \pm SD$ (h) |
|---|---|---|---|---|---|
| hGH IR | 90 ± 24 | 39 | 258 ± 26 | 100 | 2 ± 0.3 |
| Formulation 3 | 26 ± 16 | 108 ± 38 | 999 ± 294 | 77 | 66 ± 14 | where:

$C_{max}$ is the maximum serum hGH concentration,

T>1 ng/mL is the time when the serum hGH concentration is greater than 1 ng/mL,

AUC represents the area under the curve of serum hGH concentration as a function of time, RBA represents the bioavailability relative to an Immediate-Release formulation, $T_{50\% \, auc}$ represents the time required to release 50% of the total hGH released.

The microparticles release the hGH over more than 5 days with a 23% loss of bioavailability.

Comparative Example 14 in vitro Release (Test L) of hGH from Microparticles According to the Invention and Nanoparticles of PO A comparison of the release of hGH from nanoparticles of PO (Example 2) and microparticles of PO (Example 8) is made in the test L. The continuous phase is a buffered solution of albumin containing 30 mg/g.

The single FIGURE attached shows the time required to release 50% of the protein (hGH) under the concentration conditions in which the formulation is injectable:

nanoparticles containing 23 mg/g: $t_r$=40 min, i.e. 0.67 h microparticles containing 73 mg/g: $T_r$=973 min, i.e. 16.22 h The hGH contained in microparticles is released 24 times more slowly than that contained in nanoparticles.

Example 15

Preparation of Individual Flasks Containing a Lyophilized Powder of Microparticles of Polymer PO and Insulin (100 UI/Flask)

Preparation of 350 g of an Insulin Solution Concentrated to 500 UI/g (17.5 mg/g):

6.4 g of recombinant human insulin (powder) (28.6 UI/g, moisture content: 4.5%) are introduced in a glass flask. 157 g of water are added and insulin is dispersed with low magnetic stirring. 46.6 g of 0.1 N HCl are added until to obtain a clear solution of acid insulin. 69.8 g of 0.1 N sodium carbonate are then added in order to obtain a final clear solution having a pH comprised between 7 and 8. The solution is diluted to the desired concentration by adding 70.2 g of water.

Mixing with the Solution of Polymer PO:

326 g of the obtained concentrated insulin solution are slowly poured (with magnetic stirring) onto 3426 g of a solution of polymer PO (concentrated 11 mg/g). The mixture is passed through a 0.2 μm filter and is left with low stirring overnight. All following steps are effected under aseptic conditions.

Flocculation—Washing—Concentration:

The previous formulation is flocculated by the controlled addition of 377 g of 2 M $MgCl_2$ (with a ratio r of 7.2). After ageing 1 h, the suspension is washed with water by tangential microfiltration (Microza module from Pall with a specific surface area of 0.32 m²) until the osmolality is about 340 mOsm and concentrated to a PO concentration of about 27 mg/g. The pH is adjusted to 6.5 by adding 1 N NaOH solution (about 6 g) in the suspension. This gives a suspension containing about 100 UI/g of insulin (the exact value can be obtained by HPLC on a C18-grafted silica column).

Adding of Polyvinylpyrrolidone:

200 g of a stock solution of polyvinylpyrrolidone, concentrated to about 40 mg/g are obtained from an injectable polyvinylpyrrolidone powder (for example K17) and are passed through a 0.2 μm sterilising filter. 120 g of the filtered solution are then added under sterile conditions to 1200 g of the previous suspension and the mixture is stirred for about 15 min.

The obtained suspension contains about 91 UI/g of insulin.

Lyophilization:

The previous suspension is distributed in individual flasks with 100 UI per flask (about 1.1 g of the previous suspension per flask): the flasks are lyophilized under sterile conditions for un cycle of 72 h. They are then hermetically closed until they are used.

Example 16

Reconstitution of the Flasks of Microparticles/Insulin Obtained in Example 15

The suspension is extemporaneously reconstituted (before using) as follows:

1 ml of water is introduced using a syringe and a needle in a flask containing 100 UI of insulin obtained in the previous example.

The flask is manually stirred for a few seconds in order to obtain a homogeneous (milky) suspension: the suspension is withdrawn in the syringe and is ready to be injected with a 30 G needle, for example.

The reconstituted suspension contains:
23 mg/ml of polymer PO
100 UI/ml of insulin (3.5 mg/ml)
4 mg/ml of polyvinylpyrrolidone
0.18 mmol/ml of $Mg^{2+}$ (with r=2.8).

The characteristics of the reconstituted suspension are described below:

| $r = 2 \times \frac{[Mg^{2+}]}{[COO^-]}$ (according to test M) | pH | Osmolality mOsm | Size D(0.5) μm (according to test T1) | $d_{app}$(mg/ml) (according to test D) |
|---|---|---|---|---|
| 2,8 | 6.5 | 300 | 15.0 | 0.13 |

The dynamic viscosity measured at 20° C. is equal to 5 mPa·s.

Example 17

Pharmacokinetics of Insulin in the Dog after Subcutaneous Injection of a Formulation Based on Amphiphilic Polyamino Acids in the Form of Microparticles Two groups of 6 naïve beagle dogs (weighing 10.4±0.6 kg) were successively treated with one of the following formulations during a crossover trial with 2 periods:

| Formulation | Number of dogs | [insulin] (UI/g) | [PO] (mg/g) | Dose (UI/kg) | Dose Volume (μL/kg) |
|---|---|---|---|---|---|
| Lantus ® (batch 40N300) | 12 | 100 | 0 | 1 | 10 |
| Formulation 4 | 12 | 100 | 20 | 1 | 10 |

The reference of this trial, Lantus®, is a modified insulin analog (insulin glargine) provided by Sanofi-A Ventis. The modification of two amino acid residues on the primary structure of the human insulin gives to Lantus® some properties of prolonged release on a 24 h period thanks to an in situ precipitation.

Formulation 4 is prepared according to Example 16.

The glycaemia is determined by enzymatic method (hexokinase) with an automatic biochemical analyser (Advia 1650, Bayer Diagnostics).

The analysis of the pharmacokinetic results is based on the percentage of the basal glycaemia as a function of time.

The pharmacokinetic data are collated in the Table below:

where:
$C_{min}$ is the minimum percentage of the basal glycaemia, which has been observed,
$APGC_{0-36h}$ represents the area between the basal glycaemia and the percentage of the basal glycaemia as a function of time between 0 and 36 h post-dose,
$T_{50\% \; APGC}$ represents the time required to obtain 50% of the $APGC_{0-36}$h.

The administration of the reference Lantus® allows a rapid diminution of the glycaemia from the first hour. The hypoglycaemic action of insulin glargine is then maintained over a period comprised between 18 and 36 h (the glycaemia comes back to its basal level after 30 h on average).

Comparatively, the administration of formulation 4 allows also a rapid diminution of the glycaemia from the first hour. Then, the percentage of the basal glycaemia maintains a plateau until 36 h on average. $C_{min}$ obtained with formulation 4 is significantly higher than the value obtained with the reference Lantus® (p<0.005, paired and unilateral Student t-test), that could allow to considerably reduce the phases of severe hypoglycaemia in diabetic patients.

The action time of formulation 4 is clearly greater than the action time of the long action reference Lantus®E). This is illustrated by a $T_{50\% \; APGC}$ value which is significantly higher for formulation 4 (p<0.005, paired and unilateral Student t-test). No loss of $APGC_{0-36h}$ has been observed for formulation 4 in comparison with the reference Lantus®.

Example 18

Preparation of Lyophilized Powder of Microparticles of Polymer PO and of interferon α-2b Preparation of a Solution Containing 15 mg/g of Polymer PO and 0.19 mg/g d'IFN:

166 g of a solution of 16.5 mg/g polymer PO are introduced in a 500 ml flask. 2.3 g of a 0.3 M methionine solution are added. A frozen IFNα-2b solution (concentrated 2.4 mg/g) is thawed for 1 h at 25° C. and 13 g of this frozen solution are introduced in the flask comprising the polymer solution. The mixture is left for 14 h at room temperature.

| Formulation | $C_{min}$ ± SD (%) | $APGC_{0-36h}$ ± SD (% · h) | $APGC_{formulation \; 4}/APGC_{Lantus}$ ± SD (%) | T50% $_{APGC}$ ± SD (h) |
|---|---|---|---|---|
| Lantus ® | 40 ± 6 | 1250 ± 342 | — | 13.3 ± 3.1 |
| Formulation 4 | 45 ± 4 | 1389 ± 309 | 118 ± 37 | 19.7 ± 3.7 |

The solution is passed through a 0.2 μm sterilising filter. All following steps are effected under aseptic conditions.

Flocculation—Washing—Concentration:

129.5 g of the previous formulation are flocculated by the controlled addition of 148.5 g of 2 M $MgCl_2$ (with a ratio r of 7.0). The suspension is distributed in 4 flasks (about 37 g per flask) and centrifuged for 15 min at 3000 rpm/min. 30.5 g of supernatant are removed from the flasks by taking care to not touch the centrifugation residue. The residues are then washed with 17 g of sterile water in each flask. For this step, the osmolality is about 300 mOsm.

Lyophilization:

The previous suspension is distributed in trays of the Lyoguard® type (Gore®) allowing to keep sterile the suspension during the lyophilization: the trays are then lyophilized under sterile conditions for a cycle of 72 h with a laboratory freeze-dryer (Christ).

Example 19

Reconstitution of the Suspension of Microparticles Containing Interferon α-2b from the Lyophilized Powder Obtained in Example 18

In order to know the amount of powder to use for obtaining exactly 0.5 mg/g of interferon in the formulation, a preliminary reconstitution test is made and the interferon α-2b is assayed by HPLC with a C18-grafted silica column.

The suspension is extemporaneously reconstituted (before using) as follows:

13.58 g of water are added onto 1.22 g of lyophilized powder and the suspension is homogenised with a magnetic rod for 1 h.

The obtained suspension is homogeneous (milky): the suspension is withdrawn in a syringe and is ready to be injected with a 30 G needle, for example.

The reconstituted suspension contains:

46 mg/ml of polymer PO
0.5 mg/ml of interefon α-2b
0.34 mmol/ml of $Mg^{2+}$ (with r=2.6).

The characteristics of the reconstituted suspension are described below:

| $r = 2 \times \frac{[Mg^{2+}]}{[COO^-]}$ (according to test M) | pH | Osmolality mOsm | Size D(0.5) μm (according to test T1) | $d_{app}$(mg/ml) (according to test D) |
|---|---|---|---|---|
| 2,6 | 6.1 | 705 | 16.0 | 0.12 |

The dynamic viscosity measured at 20° C. is equal to 9 mPa·s.

Example 20

Pharmacokinetics of IFN in the Dog after Subcutaneous Injection of a Formulation Based on Amphiphilic Polyamino Acids in the Form of Microparticles Eight naïve beagle dogs (weighing 9±0.6 kg) were treated with the following formulations:

| Formulation | Number of dogs | [IFN] (mg/ml) | [PO] (mg/ml) | pH/ mOsm | Dose (μg/kg) | Dose Volume (ml/kg) |
|---|---|---|---|---|---|---|
| IFN IR | 4 | 0.5 | 0 | 6.45/ 354 | 60 | 0.12 |
| Formulation 5 | 4 | 0.5 | 46 | 6.1/ 705 | 60 | 0.12 |

The IFN IR corresponds to a solution of recombinant human interferon (PCGEn, batch IB05.0516 with adjusted concentration, pH and osmolality ([IFN]=0.5 mg/ml, pH=6.45, 354 mOsm).

Formulation 5 is prepared according to Example 19, from the same batch of interferon (PCGen).

The pharmacokinetic data are collated in the Table below:

| Formulation | $C_{max} \pm SD$ (ng/mL) | T > 50 pg/mL ± SD (h) | $AUC_{0-all} \pm SD$ (ng · h/ml) | RBA (%) | $T_{50\% \, auc} \pm SD$ (h) |
|---|---|---|---|---|---|
| IFN IR | 25.2 ± 0.4 | 22.6 ± 0.6 | 162.5 ± 27.2 | 100 | 5.1 ± 0.7 |
| Formulation 5 | 0.9 ± 0.6 | 219.8 ± 29.8 | 95.5 ± 47.5 | >59 | 96.7 ± 31.7 | where:
  $C_{max}$ is the maximum serum IFN concentration,
  T>5 pg/ml is the time when the serum IFN concentration is greater than 50 pg/ml,
  AUC represents the area under the curve of serum IFN concentration as a function of time,
  RBA represents the bioavailability relative to an Immediate-Release formulation,
  $T_{50\% \, auc}$ represents the time required to release 50% of the total IFN released.

The IFN IR has a rapid release profile with a maximum serum concentration of 25.2±0.4 ng/ml reached after a median time of 5 hours (range 3-5 h). The circulating IFN is no longer quantifiable beyond 24 hours.

Formulation 5 offers a major modification of the pharmacokinetic profile of the IFN with a very slow release, and a maximum serum concentration of 0.9±0.6 ng/ml (28 times lower than the concentration of the IR), reached after a median time of 108 hours (range 66-144 h). The general trend of the pharmacokinetics is a flat profile in the form of a pseudo-plateau. The level of circulating IFN returns to an unquantifiable concentration between 168 hours and more than 240 hours (7 and more than 10 days).

This formulation has a smaller AUC: 41% loss of relative bioavailability (RBA=59%). The $T_{50\% \, auc}$ is about 19 times greater than the $T_{50\% \, auc}$ of the IFN IR.

The invention claimed is:

1. A liquid pharmaceutical formulation for the prolonged release of active principle (AP), wherein the formulation comprises:
   an aqueous colloidal suspension of low viscosity comprising micrometric particles based on partially ionized polymer (PO) and multivalent ions of opposite polarity to that of the polymer in a molar ratio r,
   wherein the micrometric particles have a size, measured in a test T, of between 1 and 70 μm;
   wherein the polymer is a water-soluble, biodegradable, amphiphilic copolymer carrying hydrophobic groups (GH) and ionizable hydrophilic groups (GI) that are at least partially ionized,
   wherein the polymer is a polyamino acid whose main chain is made up of aspartic residues or glutamic residues, at least some of these residues being modified by the grafting of at least one hydrophobic group (GH) in the chain or at the end of the chain,
   wherein the polymer spontaneously forms a colloidal suspension of nanoparticles in water, at pH=7.0, under isotonic conditions,
   wherein said nanoparticles are capable of associating spontaneously and non-covalently with at least one active principle, at pH 7.0, under isotonic conditions,
   wherein the multivalent ions have a valency less than or equal to 4,
   wherein said multivalent ions are added in an amount such that the ratio r, measured in a test M is between 0.3 and 10, and wherein the ratio r is defined by the formula $$r = n \times \frac{[IM]}{[GI]},$$

and wherein
  n is a valency of said multivalent ions,
  [IM] is a molar concentration of said multivalent ions, and
  [GI] is a molar concentration of said ionizable hydrophilic groups.

2. The formulation of claim 1, wherein the micrometric particles have an apparent polymer density $d_{app}$, measured in a test D, of between 0.05 and 1.0.

3. The formulation of claim 1, wherein the release time $T_r$ of a given AP, as measured in a test L, increases relative to the release time $t_r$ of an identical injectable formulation not containing multivalent ions, as measured in the same test L, this increase being such that $T_r$ is greater than or equal to $1.1 \times t_r$.

4. The formulation of claim 1, wherein its dynamic viscosity at 20° C, for a shear gradient of 1000 s$^{-1}$, is less than or equal to 500 mPa·s.

5. The formulation of claim 1, wherein the hydrophobic groups (GH) are attached laterally to the chain.

6. The formulation of claim 5, wherein the hydrophobically modified polymer PO is defined by general formula (I) below:

$$\text{(I)}$$

in which:
  R$^1$ is H, a linear C2 to C10 or branched C3 to C10 alkyl, a benzyl radical, a terminal residue of amino acid, or —R$^4$-[GH];
  R$^2$ is H, a linear C2 to C10 or branched C3 to C10 acyl group, a pyroglutamate or —R$^4$-[GH];
  R$^3$ is H or a cationic entity selected from the group consisting of:
    metal cations selected from the subgroup consisting of: sodium, potassium, calcium and magnesium;
    organic cations selected from the subgroup consisting of: cations based on amine, cations based on oligoamine, cations based on polyamine, and cations based on amino acid(s);
    and cationic polyamino acids selected from the subgroup consisting of: polylysine and oligolysine;
  R$^4$ is a direct bond or a "spacer" based on 1 to 4 amino acid residues;

A independently is a radical —CH$_2$— or —CH$_2$—CH$_2$—;

n/(n+m) is defined as the molar grafting rate and its value is sufficiently low for PO, dissolved in water at pH=7 and at 25° C., to form a colloidal suspension of submicronic particles of PO, wherein n/(n+m) is between 1 and 15 mol%;

n+m varies from 10 to 1000; and

GH is a hydrophobic group.

7. The formulation of claim 6, wherein the hydrophobic group GH is derived from an alcohol precursor selected from the group consisting of: octanol, dodecanol, tetradecanol, hexadecanol, octadecanol, oleyl alcohol, tocopherol and cholesterol; and wherein R$^4$ is a direct bond.

8. The formulation of claim 5, wherein the PO has (have) one of general formulae (II), (III) and (IV) below:

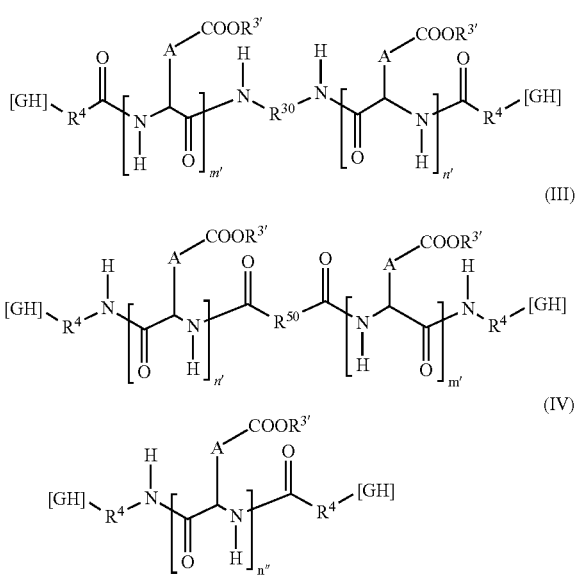

in which:

GH is a hydrophobic group;

R$^{30}$ is a linear C2 to C6 alkyl group;

R$^{3'}$ is H or a cationic entity selected from the group consisting of:

metal cations selected from the subgroup consisting of sodium, potassium, calcium and magnesium;

organic cations selected from the subgroup consisting of: cations based on amine, cations based on oligoamine, cations based on polyamine, and cations based on amino acid(s);

and cationic polyamino acids selected from the subgroup consisting of: polylysine and oligolysine;

R$^{50}$ is a C2 to C6 alkyl, dialkoxy or diamine group;

R$^4$ is a direct bond or a "spacer" based on 1 to 4 amino acid residues;

A independently is a radical —CH$_2$— or —CH$_2$—CH$_2$—; and (n'+m') or n'' is defined as the degree of polymerization and varies from 10 to 1000.

9. The formulation of claim 6, characterized in that the n groups GH of the PO each independently of one another are a monovalent radical of the formula below:

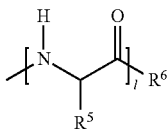

in which:

R$^5$ is selected from the group consisting of: a methyl, isopropyl, isobutyl, sec-butyl and benzyl radical;

R$^6$ is a hydrophobic radical containing from 6 to 30 carbon atoms; and l varies from 0 to 6.

10. The formulation of claim 9, wherein all or some of the hydrophobic radicals R$^6$ of the PO are independently selected from the group of radicals comprising:

a linear or branched alkoxy containing from 6 to 30 carbon atoms, a linear or branched alkoxy containing from 6 to 30 carbon atoms containing at least one heteroatom or at least one unit of unsaturation, an alkoxy containing 6 to 30 carbon atoms, having one or more fused carbocyclic rings, an alkoxy containing 6 to 30 carbon atoms, having one or more fused carbocyclic rings containing at least one unit of unsaturation and/or at least one heteroatom, and an alkoxyaryl or an aryloxyalkyl having 7 to 30 carbon atoms, an alkoxyaryl or an aryloxyalkyl having 7 to 30 carbon atoms containing at least one unit of unsaturation or at least one heteroatom.

11. The formulation of claim 9, wherein the hydrophobic radical R$^6$ of the graft of the PO is derived from an alcohol precursor selected from the group consisting of: octanol, dodecanol, tetradecanol, hexadecanol, octadecanol, oleyl alcohol, tocopherol and cholesterol.

12. The formulation of claim 1, wherein the main chain of the polyamino acid is selected from the group consisting of: an alpha-L-glutamate homopolymer, alpha-L-glutamic homopolymer, alpha-L-aspartate homopolymer, alpha-L-aspartic homopolymer, alpha-L-aspartate/alpha-L-glutamate copolymer and alpha-L-aspartic/alpha-L-glutamic copolymer.

13. The formulation of claim 1, wherein the molecular weight of the PO is between 2000 and 100,000 g/mol.

14. The formulation of claim 1, wherein the PO has anionic groups GI and wherein the multivalent ions are multivalent cations.

15. The formulation of claim 1, wherein the formulation comprises at least one stabilizer selected from the group consisting of:

nanoparticles of at least one polymer PO, PO being a water-soluble, biodegradable, amphiphilic copolymer carrying hydrophobic groups (GH) and ionizable hydrophilic groups (GI) that are at least partially ionized, and spontaneously forming a colloidal suspension of nanoparticles in water, at pH=7.0, under isotonic conditions;

polyalkylene glycols;

copolyalkylene glycols;

cellulose polymers; cellulose polymers derivatives;

esters of sorbitan and one or more fatty acids;

surfactants based on phospholipids and polyalkylene glycols;

hydrogenated or non-hydrogenated saccharides;

polyols;

gelatins;

nitrogen-containing (co)polymers;

polyvinyl alcohols (PVA);

and mixtures thereof.

16. The formulation of claim 1, wherein the AP is selected from the group consisting of proteins, glycoproteins, proteins bonded to one or more polyalkylene glycol chains; peptides, polysaccharides, liposaccharides, oligonucleotides, polynucleotides and mixtures thereof.

17. The formulation of claim 16, wherein the active principle is selected from at least one of the following families of active substances: agents for treating alcohol abuse, agents for treating Alzheimer's disease, anesthetics, agents for treating acromegaly, analgesics, antiasthmatics, agents for treating allergies, anticancer agents, anti-inflammatories, anticoagulants and antithrombotics, anticonvulsants, antiepileptics, antidiabetics, antiemetics, antiglaucomas, antihistamines, anti-infectives, antibiotics, antifungals, antivirals, antiparkinsonians, anticholinergics, antitussives, carbonic anhydrase inhibitors, cardiovascular agents, hypolipemics, antiarrhythmics, vasodilators, antianginals, antihypertensives, vasoprotectors, cholinesterase inhibitors, agents for treating central nervous system disorders, central nervous system stimulants, contraceptives, fertility promoters, labor inducers and inhibitors, agents for treating cystic fibrosis, dopamine receptor agonists, agents for treating endometriosis, agents for treating erectile dysfunctions, agents for treating fertility, agents for treating gastrointestinal disorders, immunomodulators and immunosuppressants, agents for treating memory disorders, antimigraines, muscle relaxants, nucleoside analogs, agents for treating osteoporosis, parasympathomimetics, prostaglandins, psychotherapeutic agents, sedatives, hypnotics and tranquilizers, neuroleptics, anxiolytics, psychostimulants, antidepressants, agents for treating dermatological disorders, steroids and hormones, amphetamines, anorexics, non-analgesic painkillers, antiepileptics, barbiturates, benzodiazepines, hypnotics, laxatives, psychotropics and any associations of these products.

18. The formulation of claim 1, wherein the weight fraction of AP not associated with the micrometric particles [non-associated AP], in %, is such that:
[non-associated AP]≤1.

19. The formulation of claim 1, wherein the AP is selected from the group consisting of: recombinant human growth hormone hGH, insulin and interferon α-2b.

20. The formulation of claim 1, wherein said formulation is intended for the preparation of drugs, for administration by the parenteral, mucosal, subcutaneous, intramuscular, intradermal, intraperitoneal or intracerebral route or intratumoral, or by the oral, nasal, pulmonary, vaginal or ocular route.

21. A process for the preparation of the formulation of claim 1, said process comprising the steps of:
a. taking or preparing a colloidal suspension of nanoparticles of at least one PO,
b. mixing this colloidal suspension of nanoparticles of PO with at least one AP, in aqueous solution,
c. filtering the resulting suspension,
d. adding multivalent ions of opposite polarity to that of the groups GI of the polymer PO, said multivalent ions being added in an amount such that the ratio r, defined by the formula $$r = n \times \frac{[IM]}{[GI]},$$

where
n is the valency of said multivalent ions,
[IM] is the molar concentration of multivalent ions,
[GI] is the molar concentration of ionizable groups GI, is between 0.3 and 10 and
e. if necessary, adjusting the pH or the osmolarity.

22. The process of claim 21, wherein the AP is in the form of an aqueous suspension or solution for mixing with the colloidal suspension of nanoparticles or microparticles of PO.

23. A process for the preparation of a product derived from the formulation of claim 20, wherein said process comprises the steps of:
a. preparing a suspension of micrometric particles
b. drying the suspension of micrometric particles to give a solid form, that is capable of being stored or administered.

24. A process for the preparation of the formulation of claim 20, wherein said process comprises the steps of:
a. preparing at least one derived product (loaded or not loaded with AP),
b. and reconstituting the derived product by mixing it with water or an aqueous solution S.

25. The liquid pharmaceutical formulation of claim 1, wherein the micrometric particles of PO have a size, measured in a test T, of between 2 and 40 μm.

26. The liquid pharmaceutical formulation of claim 1, wherein the multivalent ions are selected from the group consisting of $Mg^{2+}$, $Ca^{2+}$, $Zn^{2+}$, $Fe^{2+}$, $Cu^{2+}$, $Al^{3+}$, $Fe^{3+}$ and mixtures thereof.

27. The liquid pharmaceutical formulation of claim 1, wherein the molar ratio r is comprised between 0.6 and 5.0.

28. The liquid pharmaceutical formulation of claim 1, wherein the molar ratio r is comprised between 0.8 and 3.0.

29. The formulation of claim 2, wherein the micrometric particles have an apparent polymer density $d_{app}$, measured in a test D, of between 0.07 and 0.7.

30. The formulation of claim 2, wherein the micrometric particles have an apparent polymer density $d_{app}$, measured in a test D, of between 0.1 and 0.5.

31. The formulation of claim 3, wherein the release time $T_r$ of a given AP, as measured in a test L, increases relative to the release time $t_r$ of an identical injectable formulation not containing multivalent ions, as measured in the same test L, such that $T_r$ is greater than or equal to $1.5 \times t_r$.

32. The formulation of claim 4, wherein its dynamic viscosity at 20° C, for a shear gradient of $1000 \text{ s}^{-1}$, is between 2 and 200 mPa·s.

33. The formulation of claim 13, wherein the molecular weight of the PO is comprised between 5000 and 40,000 g/mol.

34. The formulation of claim 15, wherein the stabilizer is selected from the group comprising: polyethylene glycol; ethylene glycol/propylene glycol copolymer; esters of polyoxyalkylene glycol of the Tween or polysorbate type; surfactants based on phospholipids and polyethylene glycol; trehalose, sorbitol, mannitol or sucrose; propylene glycol or glycerol; hydrolyzed gelatins; nitrogen-containing (co)polymers; and mixtures thereof.

35. The formulation of claim 34, wherein the stabilizer is selected from an oleic acid ester of polyoxyethylene glycol; polyacrylamides, poly-N-vinylamides, polyvinylpyrrolidones (PVP) and poly-N-vinyllactams.

* * * * *